United States Patent
Han et al.

(10) Patent No.: US 11,498,904 B2
(45) Date of Patent: Nov. 15, 2022

(54) SUBSTITUTED BIARYL COMPOUNDS AS INDOLEAMINE 2,3-DIOXYGENASE (IDO) INHIBITORS

(71) Applicant: MERCK SHARP & DOHME CORP., Rahway, NJ (US)

(72) Inventors: Yongxin Han, Needham, MA (US); Abdelghani Achab, Melrose, MA (US); Indu Bharathan, Somerville, MA (US); Xavier Fradera, Boston, MA (US); Derun Li, West Roxbury, MA (US); Nunzio Sciammetta, Sudbury, MA (US); Wensheng Yu, Edison, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 64 days.

(21) Appl. No.: 16/761,855

(22) PCT Filed: Nov. 9, 2018

(86) PCT No.: PCT/US2018/059979
§ 371 (c)(1),
(2) Date: May 6, 2020

(87) PCT Pub. No.: WO2019/099294
PCT Pub. Date: May 23, 2019

(65) Prior Publication Data
US 2021/0317091 A1   Oct. 14, 2021

Related U.S. Application Data

(60) Provisional application No. 62/585,742, filed on Nov. 14, 2017.

(51) Int. Cl.
| | | |
|---|---|---|
| *C07D 241/12* | (2006.01) | |
| *A61K 45/06* | (2006.01) | |
| *C07D 213/56* | (2006.01) | |
| *C07D 213/64* | (2006.01) | |
| *C07D 213/76* | (2006.01) | |
| *C07D 237/08* | (2006.01) | |
| *C07D 239/26* | (2006.01) | |
| *C07D 241/18* | (2006.01) | |
| *C07D 401/04* | (2006.01) | |
| *C07D 405/10* | (2006.01) | |
| *C07D 413/04* | (2006.01) | |

(52) U.S. Cl.
CPC ............ *C07D 241/12* (2013.01); *A61K 45/06* (2013.01); *C07D 213/56* (2013.01); *C07D 213/64* (2013.01); *C07D 213/76* (2013.01); *C07D 237/08* (2013.01); *C07D 239/26* (2013.01); *C07D 241/18* (2013.01); *C07D 401/04* (2013.01); *C07D 405/10* (2013.01); *C07D 413/04* (2013.01)

(58) Field of Classification Search
CPC .. C07D 213/56; C07D 213/64; C07D 213/68; C07D 213/76; C07D 237/08; C07D 239/26; C07D 241/12; C07D 241/18; C07D 401/04; C07D 405/10; C07D 413/04
See application file for complete search history.

(56) References Cited

U.S. PATENT DOCUMENTS

| | | | |
|---|---|---|---|
| 5,086,054 A | 2/1992 | Parish | |
| 8,436,011 B2 | 5/2013 | Sanofi | |
| 2004/0186103 A1 | 9/2004 | Marzabadi et al. | |
| 2009/0156643 A1* | 6/2009 | Mita | C07C 251/48 514/340 |
| 2010/0197688 A1 | 8/2010 | Nantermet et al. | |
| 2011/0053941 A1 | 3/2011 | Mautino | |
| 2012/0157425 A1* | 6/2012 | Roth | C07D 411/04 514/210.2 |
| 2012/0220609 A1 | 8/2012 | Kuribayashi | |

(Continued)

FOREIGN PATENT DOCUMENTS

| | | | |
|---|---|---|---|
| CN | 104530029 | * | 4/2015 |
| CN | 104530029 A | | 4/2015 |

(Continued)

OTHER PUBLICATIONS

CN 104530029—Espacenet machine translation (PD 2015).*
European Search Report, PCTUS2018059979, dated Apr. 29, 2021, 8 pages.

*Primary Examiner* — Valerie Rodriguez-Garcia
(74) *Attorney, Agent, or Firm* — Baerbel R. Brown; Catherine D. Fitch

(57) ABSTRACT

Disclosed herein is a compound of formula (I), or a pharmaceutically acceptable salt thereof. Also disclosed herein are uses of a compound disclosed herein in the potential treatment or prevention of an IDO-associated disease or disorder. Also disclosed herein are compositions comprising a compound disclosed herein. Further disclosed herein are uses of a composition in the potential treatment or prevention of an IDO-associated disease or disorder.

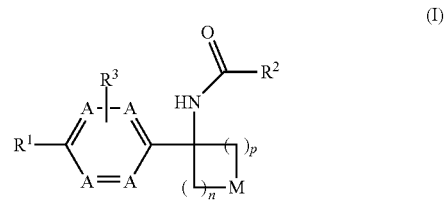

(I)

14 Claims, No Drawings

(56) References Cited

U.S. PATENT DOCUMENTS

| | | | |
|---|---|---|---|
| 2014/0255381 A1* | 9/2014 | Bourque | A61P 25/00 546/137 |
| 2014/0275023 A1 | 9/2014 | Namdev | |
| 2016/0096834 A1* | 4/2016 | Gaillard | A61P 1/02 514/210.18 |
| 2016/0159773 A1 | 6/2016 | Saitoh et al. | |
| 2017/0247336 A1 | 8/2017 | Ujjainwalla et al. | |

FOREIGN PATENT DOCUMENTS

| | | | |
|---|---|---|---|
| EP | 647612 A1 | 4/1995 | |
| EP | 757037 A2 | 2/1997 | |
| EP | 1997005868 A1 | 2/1997 | |
| FR | 2933700 A1 | 1/2010 | |
| GB | 2470833 A | 12/2010 | |
| GB | 2493914 A | 2/2013 | |
| WO | 1993013073 A1 | 7/1993 | |
| WO | 2000059874 A1 | 10/2000 | |
| WO | 2002048114 A1 | 6/2002 | |
| WO | 2003004474 A1 | 1/2003 | |
| WO | 2004056744 A1 | 7/2004 | |
| WO | 2005056529 A1 | 6/2005 | |
| WO | 2006012227 A2 | 2/2006 | |
| WO | 2006016219 A2 | 2/2006 | |
| WO | 2006133559 A1 | 12/2006 | |
| WO | 2007099326 A1 | 9/2007 | |
| WO | 2007113548 A1 | 10/2007 | |
| WO | 2007113565 A1 | 10/2007 | |
| WO | 2007117715 A2 | 10/2007 | |
| WO | 2008073936 A1 | 6/2008 | |
| WO | 2008127399 A2 | 10/2008 | |
| WO | 2010028174 A1 | 3/2010 | |
| WO | 2010028179 A1 | 3/2010 | |
| WO | 2011041461 A2 | 4/2011 | |
| WO | 2011082270 A2 | 7/2011 | |
| WO | 2012001107 A1 | 1/2012 | |
| WO | 2012059541 A1 | 5/2012 | |
| WO | 2012082817 A1 | 6/2012 | |
| WO | 2015016206 A1 | 2/2015 | |
| WO | 2015163472 A1 | 10/2015 | |
| WO | 2016057500 A1 | 4/2016 | |
| WO | 2017055469 A1 | 4/2017 | |
| WO | 2017076742 A1 | 5/2017 | |
| WO | 2017156165 A1 | 9/2017 | |
| WO | 2017192813 A1 | 11/2017 | |
| WO | 2017192844 A1 | 11/2017 | |

* cited by examiner

SUBSTITUTED BIARYL COMPOUNDS AS INDOLEAMINE 2,3-DIOXYGENASE (IDO) INHIBITORS

CROSS REFERENCE TO RELATED APPLICATIONS

The present application is the 371 national phase application of International Application No. PCT/US2018/059979, filed Nov. 9, 2018, which claims the benefit of U.S. Provisional Application No. 62/585,742, filed Novmber 14, 2017, hereby incorporated by reference in their entirety.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (EFN-γ)-inducible antimicrobial effector mechanism. IFN-γ stimulation induces activation of IDO, which leads to a depletion of Trp, thereby arresting the growth of Trp-dependent intracellular pathogens such as Toxoplasma gondii and Chlamydia trachomatis. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with inter-leukin-2 (IL2) was believed to result from IDO released by the tumor cells in response to IFN-γ secretion by the PBLs. This effect was reversed by treatment with 1-methyl-tryptophan (IMT), a specific IDO inhibitor. It was proposed that IDO activity in tumor cells may serve to impair antitumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to IMT, and a rapid, T cell-induced rejection of all allogeneic conception was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD 123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

In light of the potential role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. Compounds disclosed herein are useful in the potential treatment or prevention of IDO-related diseases.

SUMMARY OF THE INVENTION

Disclosed herein are novel compounds of formula (I), which are inhibitors of the IDO enzymes. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein is a compound of formula (I), or a pharmaceutically acceptable salt thereof:

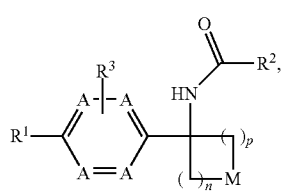

(I)

wherein:
n is selected from 1, 2 and 3;
p is selected from 0, 1 and 2;

each occurrence of A is independently selected from —CH= and —N=, provided that at least one A is —C=;

M is selected from —O—, —S— and —$CR^aR^b$—, each of $R^a$ and $R^b$ is independently selected from H, halogen, —OH, and —$C_{1-8}$ alkyl; or alternatively, $R^a$ and $R^b$ together with the carbon to which they are attached form a $C_{3-4}$ carbocyclic ring, optionally substituted with 1-2 substituents independently selected from halogen and $C_{1-4}$ alkyl;

$R^1$ is selected from:
(1) aryl, and
(2) heterocyclyl;
wherein each of the aryl of (1) and the heterocyclyl of (2) is optionally substituted with 1-3 substituents independently selected from:
(a) halogen,
(b) —$C_{3-8}$ cycloalkyl, optionally substituted with —OH,
(c) —CN,
(d) oxo,
(e) —O—$C_{1-8}$ alkyl, optionally substituted with 1-5 halogens,
(f) —O—$C_{3-8}$ cycloalkyl,
(g) —$C_{1-8}$ alkyl, optionally substituted with 1-4 substituents independently selected from halogen, —OH, —$NH_2$, $NHC(O)R^c$, and —$S(O)_2$—$C_{1-8}$ alkyl, wherein $R^c$ is selected from —$C_{1-8}$ alkyl and —$C_{3-8}$ cycloalkyl,
(h) —NH—$S(O)_2$—$R^c$, wherein $R^c$ is selected from —$C_{1-8}$ alkyl and —$C_{3-8}$ cycloalkyl,
(i) —C(O)—OH,
(j) aryl, optionally substituted with 1-3 halogens and
(k) heterocyclyl, optionally substituted with 1-3 substituents independently selected from halogen and —$C_{1-8}$ alkyl;

$R^2$ is selected from:
(1) $C_{1-8}$alkyl,
(2) —$C_{3-8}$ carbocyclyl,
(3) aryl, and
(4) heterocyclyl;
wherein the $C_{1-8}$ alkyl of (1) is optionally substituted with 1-3 substituents independently selected from:
(a) halogen,
(b) —$C_{3-8}$ cycloalkyl,
(c) —O—$C_{1-8}$ alkyl, and
(d) heterocyclyl; and
wherein each of the $C_{3-8}$ carbocyclyl of (2), the aryl of (3) and the heterocyclyl of (4) is optionally substituted with 1-3 substituents independently selected from:
(a) halogen,
(b) —$C_{3-8}$ cycloalkyl,
(c) —CN,
(d) —O—$C_{1-8}$ alkyl, optionally substituted with 1-3 halogens and
(e) —$C_{1-8}$ alkyl, optionally substituted with 1-3 substituents independently selected from halogen, —OH, and —$NH_2$; and
$R^3$ is selected from H, halogen and —$C_{1-8}$ alkyl.

In one embodiment of the compound of formula (I), or a pharmaceutically acceptable salt thereof:
n is 1;
p is 0 or 1;
M is selected from —O— and —$CR^aR^b$—, each of $R^a$ and $R^b$ is independently selected from H, halogen, —OH and —$C_{1-6}$ alkyl;

$R^1$ is selected from:
(1) aryl, and
(2) heterocyclyl;
wherein each of the aryl of (1) and the heterocyclyl of (2) is optionally substituted with 1-3 substituents independently selected from:
(a) halogen,
(b) —$C_{3-6}$ cycloalkyl, optionally substituted with —OH,
(c) —CN,
(d) —O—$C_{1-6}$ alkyl, optionally substituted with 1-3 halogens,
(e) —O—$C_{3-6}$ cycloalkyl,
(f) —$C_{1-6}$ alkyl, optionally substituted with 1-4 substituents independently selected from halogen, —OH, —$NH_2$, NHC(O)$R^c$, and —S(O)$_2$—$C_{1-6}$ alkyl, wherein $R^c$ is selected from —$C_{1-6}$ alkyl and —$C_{3-6}$ cycloalkyl,
(g) —NH—S(O)$_2$—$R^c$, wherein $R^c$ is selected from —$C_{1-6}$ alkyl and —$C_{3-6}$ cycloalkyl,
(h) —C(O)—OH, and
(i) heterocyclyl, optionally substituted with 1-3 substituents independently selected from halogen and —$C_{1-6}$ alkyl;
$R^2$ is selected from:
(1) $C_{1-6}$ alkyl, optionally substituted with 1-3 halogens,
(2) $C_{3-6}$ carbocyclyl,
(3) aryl, and
(4) heterocyclyl;
wherein each of the $C_{3-6}$ carbocyclyl of (2), the aryl of (3) and the heterocyclyl of (4) is optionally substituted with 1-3 substituents independently selected from:
(a) halogen,
(b) —$C_{3-6}$ cycloalkyl,
(c) —CN,
(d) —O—$C_{1-6}$ alkyl, optionally substituted with 1-3 halogens, and
(e) —$C_{1-6}$ alkyl, optionally substituted with 1-3 substituents independently selected from halogen, —OH, and —$NH_2$; and
$R^3$ is selected from H and halogen.

In one embodiment of the compound of formula (I), or a pharmaceutically acceptable salt thereof:
n is 1;
p is 0 or 1;
each A group is —CH=;
or alternatively, one A group is —N= and the three other A groups are each —CH=; and
M is selected from —O—, —$CH_2$—, —$CF_2$—, and —CH($CH_3$)—.

In one embodiment of the compound of formula (I), or a pharmaceutically acceptable salt thereof, $R^3$ is selected from H and halogen.

In one embodiment of the compound of formula (I), or a pharmaceutically acceptable salt thereof:
$R^1$ is selected from:
(1) phenyl, and
(2) a 5-6 membered monocyclic heterocyclyl containing one to three heteroatoms independently selected from N, O, and S;
wherein each of the phenyl of (1) and the mono-cyclic heterocyclyl of (2) is optionally substituted with 1-3 substituents independently selected from:
(a) halogen,
(b) —$C_{3-6}$ cycloalkyl optionally substituted with —OH,
(c) —CN,
(d) —O—$C_{1-6}$ alkyl, optionally substituted with 1-3 halogens,
(e) —O—$C_{3-6}$ cycloalkyl,
(f) —$C_{1-6}$ alkyl, optionally substituted with 1-4 substituents independently selected from halogen, —OH, and —S(O)$_2$—$C_{1-6}$ alkyl,
(g) —NH—S(O)$_2$—$R^c$, wherein $R^c$ is selected from —$C_{1-6}$ alkyl and —$C_{3-6}$ cycloalkyl,
(h) —C(O)—OH, and
(i) a 5-6 membered monocyclic ring containing one to three heteroatoms independently selected from N, O, and S, optionally substituted with —$C_{1-6}$ alkyl.

In one embodiment of the compound of formula (I), or a pharmaceutically acceptable salt thereof:
$R^1$ is a 5-6 membered monocyclic heterocyclyl selected from pyrazinyl, pyridazinyl, pyridinyl, and pyrimidinyl; optionally substituted with 1-3 substituents independently selected from:
(a) halogen,
(b) cyclopropyl, optionally substituted with —OH,
(c) cyclobutyl, optionally substituted with —OH,
(d) —CN,
(e) —O—$C_{1-3}$ alkyl, optionally substituted with 1-3 halogens,
(f) —O-cyclopropyl,
(g) —$C_{1-4}$ alkyl, optionally substituted with 1-4 substituents independently selected from halogen, —OH and —S(O)$_2$—$C_{1-4}$ alkyl,
(h) —C(O)—OH, and
(i) 1,2,4-oxadiazolyl, optionally substituted with —$C_{1-4}$ alkyl.

In one embodiment of the compound of formula (I), or a pharmaceutically acceptable salt thereof:
$R^2$ is selected from:
(1) $C_{1-4}$ alkyl, optionally substituted with 1-3 halogens,
(2) $C_{3-6}$ carbocyclyl, and
(3) phenyl;
wherein each of the $C_{3-6}$ carbocyclyl of (2) and the phenyl of (3) is optionally substituted with 1-3 substituents independently selected from:
(a) halogen,
(b) —$C_{3-6}$ cycloalkyl,
(c) —CN, and
(d) —$C_{1-4}$ alkyl, optionally substituted with 1-3 substituents independently selected from halogen and —OH.

In one embodiment of the compound of formula (I), or a pharmaceutically acceptable salt thereof:
$R^2$ is selected from:
(1) 5-6 membered bridged bicyclic carbocyclyl, and
(2) phenyl;
wherein each of the 5-6 membered carbocyclyl of (1) and the phenyl of (2) is optionally substituted with 1-3 substituents independently selected from:
(a) halogen,
(b) —CN, and
(c) —$C_{1-4}$ alkyl, optionally substituted with 1-3 halogens.

In one embodiment of the compound of formula (I), or a pharmaceutically acceptable salt thereof:
n is 1;
p is 0 or 1;
each A group is —CH=;
or alternatively, one A group is —N= and the three other A groups are each —CH=;
M is selected from —O—, —$CH_2$—, —$CF_2$—, and —CH($CH_3$)—;

R¹ is selected from:
(1) phenyl, and
(2) a 5-6 membered monocyclic heterocyclyl containing one to three heteroatoms independently selected from N, O, and S;
wherein each of the phenyl of (1) and the mono-cyclic heterocyclyl of (2) is optionally substituted with 1-3 substituents independently selected from:
(a) halogen,
(b) —$C_{3-6}$ cycloalkyl, optionally substituted with —OH,
(c) —CN,
(d) —O—$C_{1-6}$ alkyl, optionally substituted with 1-3 halogens,
(e) —O—$C_{3-6}$ cycloalkyl,
(f) —$C_{1-6}$ alkyl, optionally substituted with 1-4 substituents independently selected from halogen, —OH, and —S(O)$_2$—$C_{1-6}$ alkyl,
(g) —NH—S(O)$_2$—R$^c$, wherein R$^c$ is selected from —$C_{1-6}$ alkyl and —$C_{3-6}$ cycloalkyl,
(h) —C(O)—OH, and
(i) a 5-6 membered monocyclic heterocyclyl containing one to three heteroatoms independently selected from N, O, and S, optionally substituted with —$C_{1-6}$ alkyl;
R² is selected from:
(1) $C_{1-4}$ alkyl, optionally substituted with 1-3 halogens,
(2) $C_{3-6}$ carbocyclyl, and
(3) phenyl;
wherein each of the $C_{3-6}$ carbocyclyl of (2) and the phenyl of (3) is optionally substituted with 1-3 substituents independently selected from:
(a) halogen,
(b) —$C_{3-6}$ cycloalkyl,
(c) —CN, and
(d) —$C_{1-4}$ alkyl, optionally substituted with 1-3 substituents independently selected from halogen and —OH; and
R³ is selected from H and halogen.
In one embodiment of the compound of formula (I), or a pharmaceutically acceptable salt thereof:
n is 1;
p is 0 or 1;
each A group is —CH=;
or alternatively, one A group is —N= and the three other A groups are each —CH=;
M is selected from —O—, —CH$_2$—, and —CH(CH$_3$)—;
R¹ is a 5-6 membered monocyclic heterocyclyl selected from pyrazinyl, pyridazinyl, pyridinyl, and pyrimidinyl; each of which is optionally substituted with 1-3 substituents independently selected from:
(a) halogen,
(b) cyclopropyl, optionally substituted with —OH,
(c) cyclobutyl, optionally substituted with —OH,
(d) —CN,
(e) —O—$C_{1-3}$ alkyl, optionally substituted with 1-3 halogens,
(f) —O-cyclopropyl,
(g) —$C_{1-4}$ alkyl, optionally substituted with 1-4 substituents independently selected from halogen, —OH and —S(O)$_2$—$C_{1-4}$ alkyl,
(h) —C(O)—OH, and
(i) 1,2,4-oxadiazolyl, optionally substituted with —$C_{1-4}$ alkyl;
R² is selected from:
(1) a 5-6 membered bridged bicyclic carbocyclyl, and
(2) phenyl;

wherein each of the 5-6 membered carbocyclyl of (1) and the phenyl of (2) is optionally substituted with 1-3 substituents independently selected from:
(a) halogen,
(b) —CN, and
(c) —$C_{1-4}$ alkyl, optionally substituted with 1-3 halogens; and
R³ is selected from H and halogen.
In one embodiment of the compound of formula (I), or a pharmaceutically acceptable salt thereofm the compound is of formula (Ii):

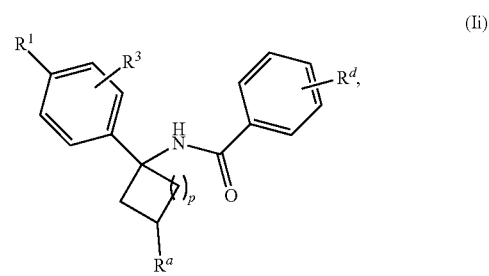

wherein:
p is 0 or 1;
R¹ is selected from:
(1) phenyl, and
(2) a 5-6 membered monocyclic heterocyclyl containing one to three heteroatoms independently selected from N, O, and S;
wherein each of the phenyl of (1) and the mono-cyclic heterocyclyl of (2) is optionally substituted with 1-3 substituents independently selected from:
(a) halogen,
(b) —$C_{3-6}$ cycloalkyl, optionally substituted with —OH,
(c) —CN,
(d) —O—$C_{1-6}$ alkyl, optionally substituted with 1-3 halogens,
(e) —O—$C_{3-6}$ cycloalkyl,
(f) —$C_{1-6}$ alkyl, optionally substituted with 1-4 substituents independently selected from halogen, —OH, and —S(O)$_2$—$C_{1-6}$ alkyl,
(g) —NH—S(O)$_2$—R$^c$, wherein R$^c$ is selected from —$C_{1-6}$ alkyl and —$C_{3-6}$ cycloalkyl,
(h) —C(O)—OH, and
(i) a 5-6 membered monocyclic heterocyclyl containing one to three heteroatoms independently selected from N, O, and S, optionally substituted with —$C_{1-6}$ alkyl;
R³ is selected from H and halogen;
R$^a$ is selected from (a) H and (b) $C_{1-4}$ alkyl; and
R$^d$ is selected from:
(a) H,
(b) halogen, and
(c) —CN.
In one embodiment of the compound of formula (I), or a pharmaceutically acceptable salt thereof:
p is 0 or 1;
R¹ is a 5-6 membered monocyclic heterocyclyl selected from pyrazinyl, pyridazinyl, pyridinyl, and pyrimidinyl; each of which is optionally substituted with 1-3 substituents independently selected from:
(a) halogen,
(b) cyclopropyl, (c) —CN,
(d) —O—$C_{1-3}$ alkyl, optionally substituted with 1-3 halogens,
(e) —O-cyclopropyl,
(f) —$C_{1-4}$ alkyl, optionally substituted with 1-4 substituents independently selected from halogen, —OH, and —S(O)$_2$—$C_{1-4}$ alkyl,
(g) —NH—S(O)$_2$—$C_{1-4}$ alkyl,
(h) —NH—S(O)$_2$-cyclopropyl,
(i) —C(O)—OH, and
(j) 1,2,4-oxadiazolyl, optionally substituted with —$C_{1-4}$ alkyl;

$R^3$ is selected from H and halogen;
$R^e$ is selected from (a) H and (b) —CH$_3$; and
$R^d$ is selected from (a) halogen and (b) —CN.

In one embodiment of the compound of formula (I), or a pharmaceutically acceptable salt thereof:
n is selected from 1, 2 and 3;
p is selected from 0, 1 and 2;
each occurrence of A is independently selected from —CH= and —N=;
M is selected from —O—, —S— and —CR$^a$R$^b$—, each of R$^a$ and R$^b$ is independently selected from H, halogen, —OH and —$C_{1-8}$ alkyl; or alternatively, R$^a$ and R$^b$ together with the carbon to which they are attached form a $C_{3-4}$ carbocyclic ring, optionally substituted with 1-2 substituents independently selected from halogen and $C_{1-4}$ alkyl;
$R^1$ is selected from:
  (1) aryl and
  (2) heterocyclyl;
  wherein each of the aryl of (1) and heterocyclyl of (2) is optionally substituted with 1-3 substituents independently selected from:
    (a) halogen,
    (b) —$C_{3-8}$ cycloalkyl optionally substituted with —OH,
    (c) —CN,
    (d) oxo,
    (e) —O—$C_{1-8}$ alkyl optionally substituted with 1-5 halogens,
    (f) —O—$C_{3-8}$ cycloalkyl,
    (g) —$C_{1-8}$ alkyl optionally substituted with 1-4 substituents independently selected from halogen, —OH, —NH$_2$, NHC(O)R$^c$ and —S(O)$_2$—$C_{1-8}$ alkyl, wherein R$^c$ is selected from —$C_{1-8}$ alkyl and —$C_{3-8}$ cycloalkyl,
    (h) —NH—S(O)$_2$—R$^c$, wherein R$^c$ is selected from —$C_{1-8}$ alkyl and —$C_{3-8}$ cycloalkyl,
    (i) —C(O)—OH,
    (j) aryl optionally substituted with 1-3 halogens and
    (k) heterocyclyl optionally substituted with 1-3 substituents independently selected from halogen and —$C_{1-8}$ alkyl;
$R^2$ is selected from:
  (1) $C_{1-8}$ alkyl,
  (2) $C_{3-8}$ carbocyclyl,
  (3) aryl and
  (4) heterocyclyl;
  wherein the $C_{1-8}$ alkyl of (1) is optionally substituted with 1-3 substituents independently selected from:
    (a) halogen,
    (b) —$C_{3-8}$ cycloalkyl,
    (c) —O—$C_{1-8}$ alkyl and
    (d) heterocyclyl; and wherein each of the $C_{3-8}$ carbocyclyl of (2), aryl of (3) and heterocyclyl of (4) is optionally substituted with 1-3 substituents independently selected from:
  (a) halogen,
  (b) —$C_{3-8}$ cycloalkyl,
  (c) —CN,
  (d) —O—$C_{1-8}$ alkyl optionally substituted with 1-3 halogens and
  (e) —$C_{1-8}$ alkyl optionally substituted with 1-3 substituents independently selected from halogen, —OH and —NH$_2$; and
$R^3$ is selected from H, halogen and —$C_{1-8}$ alkyl.

In one embodiment of a compound of formula (I), or a pharmaceutically acceptable salt thereof:
$R^1$ is selected from:
  (1) phenyl;
  (2) mono-cyclic heterocyclyl selected from a saturated, a partially unsaturated and an aromatic 4-7 membered ring containing one to four heteroatoms independently selected from N, O and S; and
  (3) a 6-12 membered fused bicyclic heterocyclyl containing one to three heteroatoms independently selected from N, O and S in either of the rings;
  wherein each of the phenyl of (1), mono-cyclic heterocyclyl of (2) and fused bicyclic heterocyclyl of (3) is optionally substituted with 1-3 substituents independently selected from:
    (a) halogen,
    (b) —$C_{3-6}$ cycloalkyl optionally substituted with —OH,
    (c) —CN,
    (d) oxo,
    (e) —O—$C_{1-6}$ alkyl optionally substituted with 1-5 halogens,
    (f) —O—$C_{3-6}$ cycloalkyl,
    (g) —$C_{1-6}$ alkyl optionally substituted with 1-4 substituents independently selected from halogen, —OH, —NH$_2$, NHC(O)$C_{1-3}$ alkyl and —S(O)$_2$—$C_{1-6}$ alkyl,
    (h) —NH—S(O)$_2$—R$^c$, wherein R$^c$ is selected from —$C_{1-6}$ alkyl and —$C_{3-6}$ cycloalkyl,
    (i) —C(O)—OH,
    (j) phenyl optionally substituted with 1-3 halogens and
    (k) an aromatic 4-7 membered monocyclic ring containing one to three heteroatoms independently selected from N, O, and S, optionally substituted with —$C_{1-6}$ alkyl.

In one embodiment of a compound of formula (I), or a pharmaceutically acceptable salt thereof:
$R^1$ is selected from:
  (1) phenyl; and
  (2) mono-cyclic heterocyclyl selected from isoxazolyl, isothiazolyl, oxadiazolyl, oxazolyl, pyrazinyl, pyrazolyl, pyridazinyl, pyridinyl, pyrimidinyl, tetrahydrofuranyl, tetrahydropyranyl, tetrazolyl and 1,2,3-thiadiazolyl;
  wherein each of the phenyl of (1) and mono-cyclic heterocyclyl of (2) is optionally substituted with 1-3 substituents independently selected from:
    (a) halogen,
    (b) cyclopropyl optionally substituted with —OH,
    (c) cyclobutyl optionally substituted with —OH,
    (d) —O—$C_{1-3}$ alkyl optionally substituted with 1-5 halogens,
    (e) —O-cyclopropyl, and
    (f) —$C_{1-4}$ alkyl optionally substituted with 1-4 substituents independently selected from halogen, —OH and —NH$_2$.

In one embodiment of a compound of formula (I), or a pharmaceutically acceptable salt thereof:
$R^2$ is selected from:
(1) phenyl,
(2) pyridinyl and
(3) pyrimidinyl;
wherein each of the phenyl of (1), pyridinyl of (2) and pyrimidinyl of (3) is optionally substituted with 1-3 substituents independently selected from:
(a) halogen,
(b) —CN,
(c) —O—$C_{1-4}$ alkyl optionally substituted with 1-3 halogens and
(d) $C_{1-4}$ alkyl optionally substituted with 1-3 halogens.

In one embodiment of a compound of formula (I), or a pharmaceutically acceptable salt thereof:
$R^2$ is selected from:
(1) phenyl,
(2) pyridinyl and
wherein each of the phenyl of (1) and pyridinyl of (2) is optionally substituted with 1-3 substituents independently selected from:
(a) halogen,
(b) —CN,
(c) —O—$CHF_2$,
(d) —O—$CF_3$,
(e) —$CH_3$,
(f) —$CH_2F$,
(g) —$CHF_2$, and
(h) —$CF_3$.

In one embodiment of a compound of formula (I), or a pharmaceutically acceptable salt thereof:
n is 1 or 2;
p is 0 or 1;
each A group is —CH=; or alternatively, one A group is —N= and three other A groups are each —CH=;
M is selected from —O—, —S—, —$CH_2$—, —$C(CH_3)_2$—, —$C(CH_3)F$—, —CHF—, —$CF_2$— and

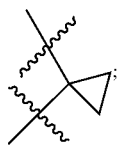 [SMILES: *C1(*)CC1]

$R^1$ is selected from:
(1) phenyl,
(2) pyridinyl, and
(3) pyrimidinyl;
wherein each of the phenyl of (1), pyridinyl of (2) and pyrimidinyl of (3) is optionally substituted with 1-3 substituents independently selected from:
(a) halogen,
(b) cyclopropyl optionally substituted with —OH,
(c) cyclobutyl optionally substituted with —OH,
(d) —O—$C_{1-3}$ alkyl optionally substituted with 1-5 halogens,
(e) —O-cyclopropyl, and
(f) —$C_{1-4}$ alkyl optionally substituted with 1-4 substituents independently selected from halogen, —OH and —$NH_2$;
$R^2$ is selected from:
(1) phenyl, and
(2) pyridinyl;

wherein each of the phenyl of (1) and pyridinyl of (2) is optionally substituted with 1-3 substituents independently selected from:
(a) halogen,
(b) —CN,
(c) —O—$C_{1-4}$ alkyl optionally substituted with 1-3 halogens and
(d) $C_{1-4}$ alkyl optionally substituted with 1-3 halogens; and
$R^3$ is H.

In one embodiment of a compound of formula (I), or a pharmaceutically acceptable salt thereof:
n is 1;
p is 1;
each A group is —CH=; or alternatively, one A group is —N= and three other A groups are each —CH=;
M is selected from —O—, —$CH_2$—, —$CF_2$— and

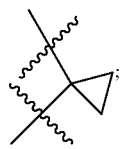 [SMILES: *C1(*)CC1]

$R^1$ is selected from:
(1) phenyl and
(2) pyridinyl;
wherein each of the phenyl of (1) and pyridinyl of (2) is optionally substituted with 1-3 substituents independently selected from:
(a) halogen,
(b) cyclopropyl optionally substituted with —OH,
(c) —O—$CH_3$,
(d) —O—$CH(CH_3)_2$,
(e) —O—$CF_3$,
(f) —O—$CHF_2$,
(g) —$CHF_2$,
(h) —$CF_3$,
(i) —$CH_2CF_3$,
(j) —$CH_2OH$,
(k) —$CH_2CH_3$,
(l) —$CH(CH_3)OH$,
(m) —$CH_2CH_2OH$,
(n) —$CH(CHF_2)OH$,
(o) —$C(CH_3)_2OH$,
(p) —$CH(CF_3)OH$, and
(q) —O-cyclopropyl;
$R^2$ is selected from:
(1) phenyl, and
(2) pyridinyl;
wherein each of the phenyl of (1) and pyridinyl of (2) is optionally substituted with 1-3 substituents independently selected from:
(a) halogen,
(b) —CN, and
(c) —$CF_3$; and
$R^3$ is H.

In one embodiment of a compound of formula (I), or a pharmaceutically acceptable salt thereof, the compound is of formula (Ia) or (Ib):

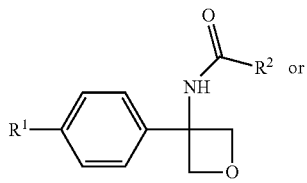
(Ia)

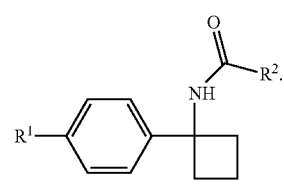
(Ib)

In one embodiment of a compound of formula (I), or a pharmaceutically acceptable salt thereof, the compound is of formula (Ic) or (Id):

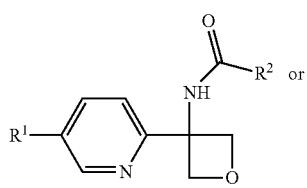
(Ic)

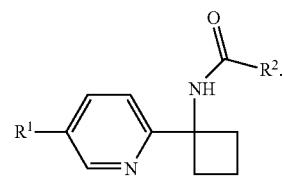
(Id)

In one embodiment of a compound of formula (I), or a pharmaceutically acceptable salt thereof, the compound is of formula (Ie) or (If):

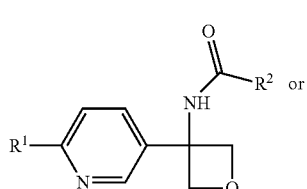
(Ie)

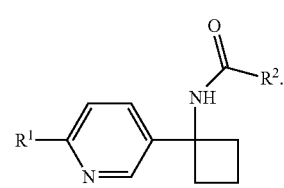
(If)

In one embodiment of a compound of formula (I), or a pharmaceutically acceptable salt thereof, the compound is of formula (Ig) or (Ih):

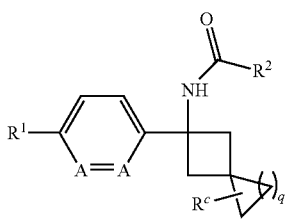
(Ig)

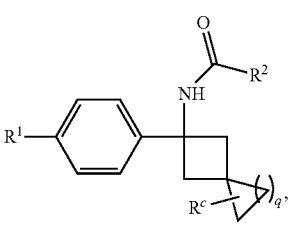
(Ih)

wherein q is 1 or 2; each A is independently —CH= or —N=; and $R^c$ is H, halogen or $C_{1-3}$ alkyl.

In one embodiment of a compound of formula (Ia), (Ib), (Ic), (Id), (Ie), (If), (Ig), or (Ih), or a pharmaceutically acceptable salt thereof:

$R^1$ is selected from:
(1) phenyl; and
(2) mono-cyclic heterocyclyl selected from isoxazolyl, isothiazolyl, oxadiazolyl, oxazolyl, pyrazinyl, pyrazolyl, pyridazinyl, pyridinyl, pyrimidinyl, tetrahydrofuranyl, tetrahydropyranyl, tetrazolyl and 1,2,3-thiadiazolyl;
wherein each of the phenyl of (1) and mono-cyclic heterocyclyl of (2) is optionally substituted with 1-3 substituents independently selected from:
(a) halogen,
(b) cyclopropyl optionally substituted with —OH,
(c) cyclobutyl optionally substituted with —OH,
(d) —O—$C_{1-3}$ alkyl optionally substituted with 1-5 halogens,
(e) —O-cyclopropyl, and
(f) —$C_{1-4}$ alkyl optionally substituted with 1-4 substituents independently selected from halogen, —OH and —$NH_2$; and $R^2$ is selected from:
(1) phenyl and
(2) pyridinyl;
wherein each of the phenyl of (1) and pyridinyl of (2) is optionally substituted with 1-3 substituents independently selected from:
(a) halogen,
(b) —CN,
(c) —O—$C_{1-3}$ alkyl optionally substituted with 1-3 halogens and
(d) $C_{1-3}$ alkyl optionally substituted with 1-3 halogens.

In one embodiment of a compound of formula (Ia), (Ib), (Ic), (Id), (Ie), (If), (Ig), or (Ih), or a pharmaceutically acceptable salt thereof:

$R^1$ is selected from:
(1) phenyl and
(2) pyridinyl;
wherein each of the phenyl of (1) and pyridinyl of (2) is optionally substituted with 1-3 substituents independently selected from:
(a) halogen,
(b) cyclopropyl optionally substituted with —OH, (c) —O—CH$_3$,
(d) —O—CF$_3$,
(e) —O—CHF$_2$,
(f) —O—CF$_2$CF$_3$,
(g) —CH$_3$,
(h) —CH$_2$F,
(i) —CHF$_2$,
(j) —CF$_3$,
(k) —CH$_2$CF$_3$,
(l) —CH$_2$OH,
(m) —CH(CH$_3$)OH,
(n) —CH$_2$CH$_2$OH,
(o) —CH(CHF$_2$)OH,
(p) —C(CH$_3$)$_2$OH,
(q) —C(CF$_3$)$_2$OH; and R$^2$ is selected from:
(1) phenyl and
(2) pyridinyl;
wherein each of the phenyl of (1) and pyridinyl of (2) is optionally substituted with 1-3 substituents independently selected from:
(a) halogen,
(b) —CN,
(c) —O—CHF$_2$,
(d) —O—CF$_3$,
(e) —CH$_3$,
(f) —CH$_2$F,
(g) —CHF$_2$, and
(h) —CF$_3$.

In one embodiment of a compound of formula (Ia), (Ib), (Ic), (Id), (Ie), (If), (Ig), or (Ih), or a pharmaceutically acceptable salt thereof:
R$^1$ is selected from:
(1) phenyl and
(2) pyridinyl;
wherein each of the phenyl of (1) and pyridinyl of (2) is optionally substituted with 1-3 substituents independently selected from:
(a) halogen,
(b) cyclopropyl optionally substituted with —OH,
(c) —O—CH$_3$,
(d) —O—CF$_3$,
(e) —O—CHF$_2$,
(f) —O—CF$_2$CF$_3$,
(g) —CH$_3$,
(h) —CH$_2$F,
(i) —CHF$_2$,
(j) —CF$_3$,
(k) —CH$_2$CF$_3$,
(l) —CH$_2$OH,
(m) —CH(CH$_3$)OH,
(n) —CH$_2$CH$_2$OH,
(o) —CH(CHF$_2$)OH,
(p) —C(CH$_3$)$_2$OH,
(q) —C(CF$_3$)$_2$OH, and R$^2$ is phenyl, optionally substituted with 1-3 substituents independently selected from:
(a) halogen,
(b) —CN,
(c) —O—CHF$_2$,
(d) —O—CF$_3$,
(e) —CH$_3$,
(f) —CH$_2$F,
(g) —CHF$_2$, and
(h) —CF$_3$.

In one embodiment, a compound disclosed herein is selected from the group consisting of the compounds exemplified in Examples 1 to 60; or a pharmaceutically acceptable salt, solvate or hydrate thereof.

Also disclosed herein is a pharmaceutical composition comprising a compound disclosed herein and at least one pharmaceutically acceptable carrier.

Also disclosed herein is a method of inhibiting activity of indoleamine 2,3-dioxygenase (IDO) comprising contacting IDO with a compound disclosed herein, or a pharmaceutically acceptable salt, solvate or hydrate thereof.

Also disclosed herein is a method of inhibiting immunosuppression in a patient comprising administering to said patient an effective amount of a compound disclosed herein, or a pharmaceutically acceptable salt, solvate or hydrate thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound disclosed herein, or a pharmaceutically acceptable salt, solvate or hydrate thereof.

Also disclosed herein is a method of treating melanoma in a patient comprising administering to said patient an effective amount of a compound disclosed herein, or a pharmaceutically acceptable salt, solvate or hydrate thereof.

Further disclosed herein is a compound disclosed herein, or a pharmaceutically acceptable salt thereof, for use in therapy. In one embodiment, disclosed herein is the use of a compound disclosed herein, or a pharmaceutically acceptable salt, solvate or hydrate thereof, for the preparation of a medicament for use in therapy.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "C$_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a C$_{4-7}$ cycloalkyl or C$_{4-7}$ cycloalkenyl ring. Aryl groups may be optionally substituted with one or more substituents as defined herein. Bonding can be through any of the carbon atoms of any ring.

"Carbocyclyl" refers to a nonaromatic (i.e., saturated or partially unsaturated) monocyclic carbocyclic radical or a fused bicyclic, bridged bicyclic, or spirocyclic carbocyclic radical having the specified ring carbon atoms. For example, "C$_{3-8}$ carbocyclyl" refers to a nonaromatic 3 to 8-membered monocyclic carbocyclic radical or a nonaromatic 3 to 8-membered fused bicyclic, bridged bicyclic, or spirocyclic carbocyclic radical. The carbocycle may be attached by any atom of the cycle which results in the creation of a stable structure. Non-limiting examples of 3 to 8-membered monocyclic carbocycles include cyclopropyl, cyclobutyl, cyclopentyl, cyclopentenyl, cyclohexyl, cyclohexenyl, cycloheptanyl and cycloheptenyl. Non-limiting examples of 6 to 8-membered fused bicyclic carbocyclic radicals include, but are not limited to, bicyclo[3.3.0]octane. Non-limiting examples of 5 to 8-membered bridged bicyclic carbocyclic radicals include, but are not limited to, bicyclo[1.1.1]pentanyl, bicyclo[2.2.2]heptanyl, bicyclo[2.2.2]octanyl, and bicyclo[3.2.1]octanyl. Non-limiting examples of 6 to 8-membered spirocyclic carbocyclic radicals include, but are not limited to, spiro[3,3]heptanyl and spiro[3,4]octanyl. In one embodiment, a carbocyclyl is a $C_{3-8}$ cycloalkyl. In one embodiment, a carbocyclyl is a 5-6 membered bridged bicyclic carbocyclyl. In another embodiment, a carbocyclyl is bicyclo[1.1.1]pentanyl.

"Cycloalkyl" refers to a monocyclic saturated carbocyclic ring having the specified number of ring carbon atoms. For example, $C_{3-8}$ cycloalkyl refers to a cycloalkyl group as defined herein having 3 to 8 carbon atoms. Examples of cycloalkyl include, but are not limited to, cyclopropyl, cyclobutyl, cyclopentyl, cyclohexyl and cycloheptanyl. Cycloalkyl groups may be optionally substituted with one or more substituents as defined herein.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydropyranyl, dihydropyrazinyl, dihydropyridazinyl, dihydropyridinyl, dihydropyrimidinyl, dihydrotriazolyl, furanyl, imidazolyl, isothiazolyl, isoxazolyl, oxadiazolyl, oxazolyl, oxoimidazolidinyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl.

In one embodiment, the heterocyclyl is selected from pyrazinyl, pyridazinyl, pyridinyl, and pyrimidinyl. In another embodiment, the heterocyclyl is pyridinyl.

In one embodiment, the heterocyclyl is 1,2,4-oxadiazolyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound disclosed herein, including a salt, solvate or hydrate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound disclosed herein.

Optical Isomers—Diastereomers—Geometric Isomers—Tautomers

Included herein are various isomers of the compounds disclosed herein. The term "isomers" refers to compounds that have the same composition and molecular weight but differ in physical and/or chemical properties. The structural difference may be in constitution (geometric isomers) or in the ability to rotate the plane of polarized light (stereoisomers).

With regard to stereoisomers, a compound disclosed herein may have one or more asymmetric carbon atom and may occur as mixtures (such as a racemic mixture) or as individual enantiomers or diastereomers. All such isomeric forms are included herein, including mixtures thereof. If a compound disclosed herein contains a double bond, the substituent may be in the E or Z configuration. If a compound disclosed herein contains a disubstituted cycloalkyl, the cycloalkyl substituent may have a cis- or trans-configuration. All tautomeric forms are also intended to be included.

Any asymmetric atom (e.g., carbon) of a compound disclosed herein, can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound disclosed herein, can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —CH$_2$C(O)— groups (keto forms) may undergo tautomerism to form hydroxyl —CH═C(OH)— groups (enol forms). Both keto and enol forms, individually as well as mixtures thereof, are included within the scope of the present invention.

Isotopic Variations

Compounds disclosed herein, include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2$H (i.e., Deuterium or "D"), $^3$H, $^{11}$C, $^{13}$C, $^{14}$C, $^{13}$N, $^{15}$N, $^{15}$O, $^{17}$O, $^{18}$O, $^{32}$P, $^{35}$S, $^{18}$F, $^{123}$I, $^{125}$I and $^{36}$Cl. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}$C, $^{81}$F, $^{15}$O and $^{13}$N may be particularly desirable for PET or SPECT studies.

Isotopically-labeled compounds disclosed herein, can generally be prepared by conventional techniques known to those skilled in the art. Furthermore, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound disclosed herein is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids.

Methods of Use

Compounds disclosed herein can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt, solvate or hydrate thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt, solvate or hydrate thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt, solvate or hydrate thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound disclosed herein.

One embodiment of the present invention provides for a method of treating a disease or disorder associated with IDO enzyme activity comprising administration of an effective amount of a compound disclosed herein to a subject in need of treatment thereof. In one embodiment, the disease or disorder associated with an IDO enzyme is a cell proliferation disorder.

In one embodiment, disclosed herein is the use of a compound disclosed herein in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound disclosed herein, or a pharmaceutically acceptable salt, solvate or hydrate thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from a combination of a specified compound in a specified amount. Such term is intended to encompass a dosage form comprising a compound disclosed herein, or a pharmaceutically acceptable salt, solvate or hydrate thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound disclosed herein, or a pharmaceutically acceptable salt, solvate or hydrate thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound disclosed herein. When prepared in unit dosage form, the composition of the invention typically contains from about 0.1 mg to 2 grams, or more specifically, 0.1 mg to 500 mg, or even more specifically, 0.2 mg to 100 mg, of a compound disclosed herein, or a pharmaceutically acceptable salt, solvate or hydrate thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution;

while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound disclosed herein and one or more other active agent(s) together in the same pharmaceutical composition, or a compound disclosed herein, and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound disclosed herein, and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound disclosed herein, for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound disclosed herein.

The invention also provides the use of a compound disclosed herein for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound disclosed herein. The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)-((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-yl)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinon (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE).

EXPERIMENTAL

The following synthetic schemes and examples are intended to be illustrative only and not limiting in any way. Abbreviations used are those conventional in the art or the following.

ACN acetonitrile
aq. aqueous
Boc tert-butyloxycarbonyl
Boc$_2$O di-tert-butyl dicarbonate
Calc'd calculated
Cu(I)I copper(I) iodide
CV column volume
° C. degree celsius
Celite diatomaceous earth used as a filtration medium
DAST (dimethylamino)sulfur trifluoride
DCM dichloromethane
DIEA N,N-diisopropylethylamine
DMA dimethylamine
DMF N,N-dimethylformamide
DMSO dimethylsulfoxide
dppf 1,1'-bis(diphenylphosphino)ferrocene
EDC N-(3-dimethylaminopropyl)-N'-ethylcarbodiimide hydrochloride EI electron ionization
EMEM Eagle's minimal essential medium
Et ethyl
Et$_2$O diethyl ether
Et$_3$N triethylamine
EtOAc ethyl acetate
EtOH ethanol
g gram
h hour(s)
HATU 1-[bis(dimethylamino)methylene]-1H-1,2,3-triazolo[4,5-b]pyridinium 3-oxid-hexafluorophosphate
HCl hydrochloric acid
HPLC high pressure liquid chromatography
K$_3$PO$_4$ potassium phosphate tribasic
kg kilogram
KO$^t$Bu potassium tert-butoxide
L liter
LC liquid chromatography
LCMS liquid chromatography and mass spectrometry
LDA lithium diisopropylamide
LiHMDS lithium bis(trimethylsilyl)amide
LiOH lithium hydroxide
M molar
Me methyl
MeOH methanol
mg miligram
mmol milimole
MS mass spectrometry
MTBE methyl tert-butyl ether
min minute(s)
mL milliliter(s)
m/z mass to charge ratio
nm nanometer
nM nanomolar
N normal
N$_2$ nitrogen
Na$_2$SO$_4$ sodium sulfate
NaH sodium hydride
NaHCO$_3$ sodium bicarbonate
NaHMDS sodium bis(trimethylsilyl)amide
NaN$_3$ sodium azide
NaOH sodium Hydroxide
NH$_4$Cl ammonium chloride OTf trifluoromethanesulfonate
Pd$_2$(dba)$_3$ tris(dibenzylideneacetone)dipalladium(0)
Pd(dppf)$_2$Cl$_2$ [1,1'-bis(diphenylphosphino)ferrocene]dichloropalladium(II)
Pd(dtbpf)Cl$_2$ [1,1'-bis(di-tert-butylphosphino)ferrocene] dichloropalladium(II)
PE petroleum ether
PG protecting group
PMP P-methoxyphenyl
POCl$_3$ phosphorus oxychloride
PS polystyrene
RPMI Roswell Park Memorial Institute
RT or rt room temperature
sat. saturated
T$_3$P propylphosphonic anhydride solution
t-BuOH tert-butanol
TBAF tetrabutylammonium fluoride
TEA triethyl amine
TFA trifluoroacetic acid
THF tetrahydrofuran
TLC thin layer chromatography
uL microliter(s)
XPhos Pd G2 chloro(2-dicyclohexylphosphino-2',4',6'-triisopropyl-1,1'-biphenyl)[2-(2'-amino-1,1'-biphenyl)] palladium(II)

General Synthetic Schemes

The compounds of formula (I) may be prepared by methods known in the art of organic synthesis as set forth in part by the following synthetic schemes and synthetic procedures and conditions for the illustrative intermediates and examples.

In the schemes described below, it is well understood that protecting groups for sensitive or reactive groups are employed where necessary in accordance with general principles of chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art.

Scheme 1

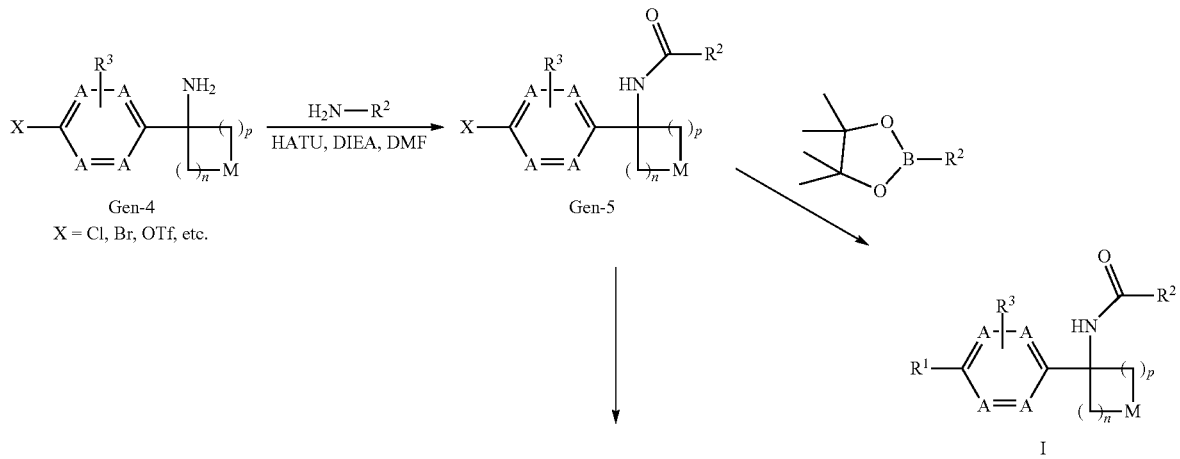

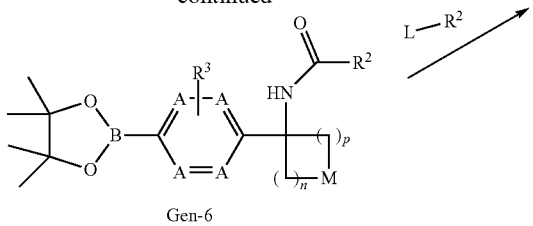

Gen-6

The compounds of formula I can be prepared by Scheme 1. An appropriate amine of general structure Gen-4 is coupled with an appropriate carboxylic acid R²—COOH or acid chloride R²—COCl under standard amide coupling conditions to give amide intermediate Gen-5. Gen-5 then reacts with an appropriate boronic acid, boronic acid pinacol ester, silicon containing agent, zincate, stannane or appropriate metallic agents under the Suzuki, Negishi, Stille, or other coupling conditions to give compounds of formula I. Alternatively, Gen-5 is converted to the corresponding boronic acid pinacol ester Gen-6 by reacting with bis(pinacolato)diboron (B2pin2) under Pd-catalyzed cross-coupling conditions. Reaction of Gen-6 with an appropriate halide, triflate, etc. under the Suzuki coupling conditions affords the compounds of formula I.

The compounds described herein may be made from commercially available starting materials or synthesized using known organic, inorganic, and/or enzymatic processes.

$^1$H NMR spectra were obtained on a Bruker Ultra Shield spectrometer at 600 MHz or a Varian 500 spectrometer at 499 MHz with tetramethylsilane used as an internal reference. LC/MS spectra were obtained on Agilent 6120 Quadrupole LC/MS spectrometers using electrospray ionization.

EXAMPLES

Example 1: 4-Cyano-N-(1-(4-(6-isopropoxypyridin-3-yl)phenyl)cyclobutyl)benzamide

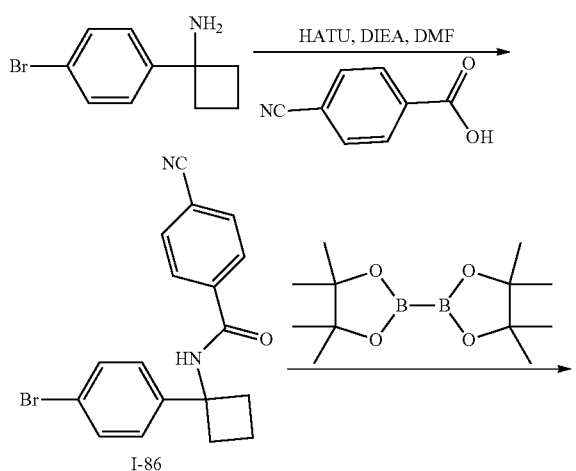

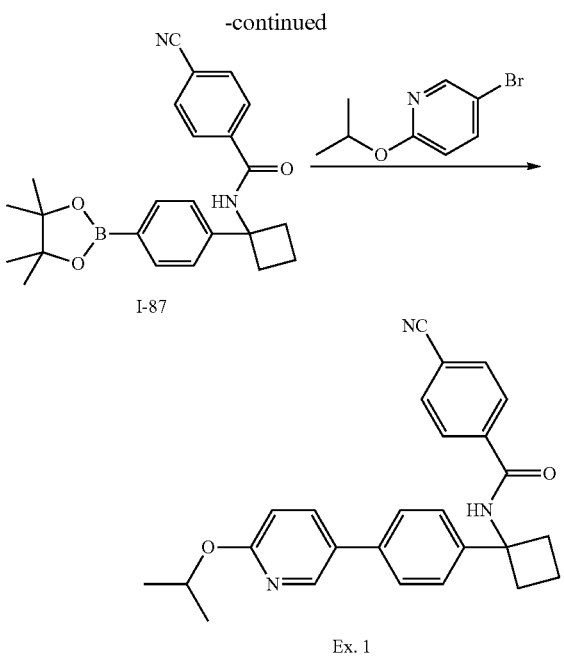

Step 1: Synthesis of N-(1-(4-bromophenyl)cyclobutyl)-4-cyanobenzamide (I-86)

To a 40 mL vial was charged with 4-cyanobenzoic acid (1952 mg, 13.27 mmol) in DMF (10.0 ml) and HATU (6054 mg, 15.92 mmol) with stirring and the reaction mixture was stirred for a few minutes. To it was added 1-(4-bromophenyl) cyclobutanamine (3000.0 mg, 13.27 mmol) and DIEA (6.95 ml, 39.8 mmol) and the reaction mixture was stirred for 12 h at RT. The reaction mixture was diluted with EtOAc and washed with 1N aq. HCl (3×), water, brine and aq. NaHCO₃. The organic layer was dried over Na₂SO₄, filtered and the filtrate was concentrated. The residue was purified by chromatography (Isco CombiFlash system, using 80 g RediSep silica gel gold column, and 0-20% MeOH/DCM as eluent) to afford compound I-86. MS (ESI) [M+H]⁺: m/z 355.

Step 2: 4-Cyano-N-(1-(4-(4,4,5,5-tetramethyl-1,3,2-dioxaborolan-2-yl)phenyl)cyclobutyl)benzamide (I-87)

To a dry round bottom flask was charged with I-86 (1500.0 mg, 4.22 mmol), bis(pinacolato)diboron (2788 mg, 10.98 mmol), potassium acetate (1227 mg, 12.50 mmol) and PdCl₂(dppf) (345 mg, 0.422 mmol) in dioxane (15.0 ml). The mixture was then evacuated and back filled with nitrogen (3×). The mixture was heated to 80° C. for 4 h, and was then cooled to RT and filtered through a Celite pad. The filtrate was concentrated in vacuo to give a residue which was dissolved in dichloromethane. After washing with water (3×) and brine (3×), the dichloromethane layer was dried over anhydrous $Na_2SO_4$ and concentrated in vacuo to give a crude product which was purified by column chromatography (silica gel, EtOAc/Hexane, 12 to 100%) to afford compound I-87. MS (ESI) [M+H]$^+$: m/z 403.

Step 3: 4-Cyano-N-(1-(4-(6-isopropoxypyridin-3-yl)phenyl)cyclobutyl)benzamide

5-Bromo-2-isopropoxypyridine (48.3 mg, 0.224 mmol), compound I-87 (30.0 mg, 0.075 mmol) and 1,1′-bis(di-tert-butylphosphino)-ferrocene palladium dichloride (4.86 mg, 7.46 μmol) were dissolved in 1,4-dioxane (2.0 ml) in a 20 mL round bottom flask, and sodium carbonate (0.075 ml, 0.149 mmol) was added. The reaction mixture was evacuated and refilled with nitrogen 3 times and heated at 80° C. for 4 h. The reaction mixture was cooled to RT and filtered through a Celite pad and concentrated. The crude material was purified by mass-directed reversed phase chromatography (ACN/water gradient with 0.1% TFA modifier) to afford the title compound. MS (ESI) [M+H]$^+$: m/z 412. $^1$H NMR (499 MHz, DMSO-d$_6$) δ 9.34 (s, 1H), 8.44 (d, J=1.9 Hz, 1H), 8.03 (d, J=8.2 Hz, 2H), 7.96 (d, J=8.4 Hz, 2H), 7.60 (d, J=8.2 Hz, 2H), 7.55 (d, J=8.2 Hz, 2H), 6.82 (d, J=8.6 Hz, 2H), 5.28 (dt, J=12.3, 6.1 Hz, 1H), 2.60 (dt, J=19.4, 6.8 Hz, 2H), 2.05 (dd, J=12.2, 8.4 Hz, 2H), 1.93-1.81 (m, 2H), 1.31 (d, J=6.1 Hz, 6H).

Hereinafter, the reaction conditions in this step are referred to as the standard Suzuki cross-coupling conditions.

Example 2: N-(1-(4-(2-Chloro-6-isopropoxypyridin-3-yl)phenyl)cyclobutyl)-4-cyanobenzamide

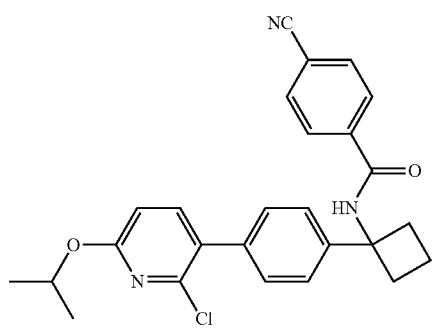 [SMILES: CC(C)Oc1ccc(-c2ccc(C3(NC(=O)c4ccc(C#N)cc4)CCC3)cc2)c(Cl)n1]

The title compound was prepared in a manner analogous to the synthesis of Example 1 except 3-bromo-2-chloro-6-isopropoxypyridine was used. MS (ESI) [M+H]$^+$: m/z 446. $^1$H NMR (499 MHz, DMSO-d6) δ 9.35 (s, 1H), 8.05 (d, J=8.2 Hz, 2H), 7.97 (d, J=8.2 Hz, 2H), 7.76 (d, J=8.3 Hz, 1H), 7.55 (d, J=8.2 Hz, 2H), 7.41 (d, J=8.1 Hz, 2H), 6.85 (d, J=8.3 Hz, 1H), 5.20 (dt, J=12.3, 6.1 Hz, 1H), 2.63 (td, J=17.8, 16.1, 10.1 Hz, 2H), 2.15-1.98 (m, 2H), 1.96-1.78 (m, 2H), 1.33 (s, 3H), 1.31 (s, 3H).

Example 3: 4-Cyano-N-(1-(4-(6-methoxy-4-methylpyridin-3-yl)phenyl)cyclobutyl)benzamide

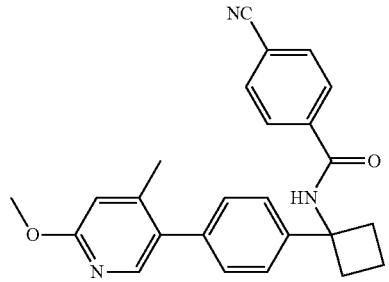 [SMILES: COc1cc(C)c(-c2ccc(C3(NC(=O)c4ccc(C#N)cc4)CCC3)cc2)cn1]

4-Cyano-N-(1-(4-(6-methoxy-4-methylpyridin-3-yl)phenyl)cyclobutyl)benzamide was prepared in a manner analogous to the synthesis of Example 1 except 5-bromo-2-methoxy-4-methylpyridine was used. MS (ESI) [M+H]$^+$: m/z 398. $^1$H NMR (499 MHz, DMSO-d6) δ 9.33 (s, 1H), 8.05 (d, J=8.2 Hz, 2H), 8.00-7.94 (m, 3H), 7.55 (d, J=8.1 Hz, 2H), 7.33 (d, J=8.0 Hz, 2H), 6.78 (s, 1H), 3.86 (s, 3H), 2.62 (dt, J=23.3, 6.9 Hz, 2H), 2.23 (s, 3H), 2.11-1.84 (m, 2H), 1.20 (dd, J=28.4, 12.8 Hz, 2H).

Example 4: 4-Cyano-N-(1-(4-(6-(difluoromethoxy)pyridin-3-yl)phenyl)cyclobutyl)benzamide

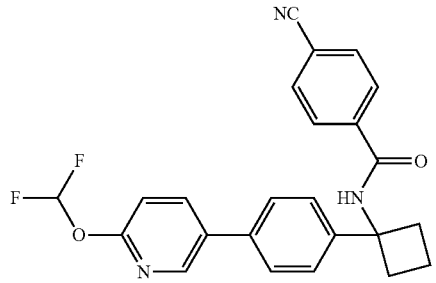 [SMILES: N#Cc1ccc(C(=O)NC2(c3ccc(-c4ccc(OC(F)F)nc4)cc3)CCC2)cc1]

The title compound was prepared in a manner analogous to the synthesis of Example 1. MS (ESI) [M+H]$^+$: m/z 420. $^1$H NMR (499 MHz, DMSO-d6) δ 9.36 (s, 1H), 8.64-8.49 (m, 1H), 8.20 (dd, J=8.5, 2.2 Hz, 1H), 8.03 (d, J=8.2 Hz, 2H), 7.96 (d, J=8.2 Hz, 2H), 7.66 (d, J=8.2 Hz, 2H), 7.59 (d, J=8.4 Hz, 2H), 7.18 (d, J=8.5 Hz, 1H), 2.61 (dt, J=18.2, 6.8 Hz, 2H), 2.06 (dd, J=10.4, 6.6 Hz, 2H), 1.96-1.78 (m, 2H).

Example 5: 4-Cyano-N-(1-(4-(6-cyclopropoxypyridin-3-yl)phenyl)cyclobutyl)benzamide

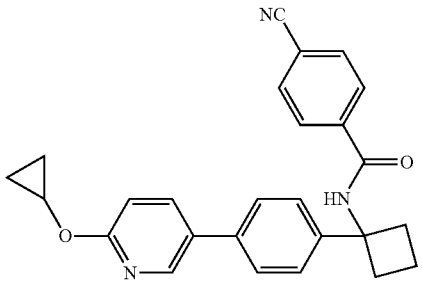 [SMILES: N#Cc1ccc(C(=O)NC2(c3ccc(-c4ccc(OC5CC5)nc4)cc3)CCC2)cc1]

The title compound was prepared in a manner analogous to the synthesis of Example 1 except 5-bromo-2-cyclopropoxypyridine was used. MS (ESI) [M+H]$^+$: m/z 410. $^1$H NMR (499 MHz, DMSO-d6) δ 9.35 (s, 1H), 8.49 (s, 1H), 8.07-7.99 (m, 2H), 7.96 (d, J=8.2 Hz, 2H), 7.68-7.52 (m, 4H), 6.94 (d, J=8.6 Hz, 2H), 4.23 (dd, J=5.9, 3.1 Hz, 1H), 2.91-2.53 (m, 4H), 1.97 (ddd, J=94.0, 16.3, 10.0 Hz, 2H), 0.98-0.55 (m, 4H).

Example 6: 4-Cyano-N-(1-(4-(6-cyclopropylpyridin-3-yl)-3-fluorophenyl)cyclobutyl)benzamide

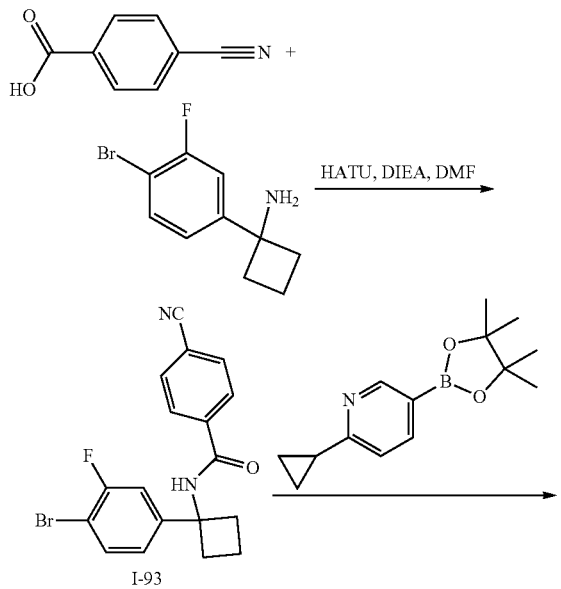

Step 1: Synthesis of N-(1-(4-bromo-3-fluorophenyl)cyclobutyl)-4-cyanobenzamide (93)

To a 20 mL vial charged with 4-cyanobenzoic acid (275.0 mg, 1.869 mmol) in DMF (5.0 ml) was added with stirring HATU (853 mg, 2.243 mmol), and the reaction mixture was stirred for a few minutes at RT. To it was added 1-(4-bromo-3-fluorophenyl)cyclobutanamine-HCl (524 mg, 1.869 mmol), DIEA (1.959 ml, 11.21 mmol), and the reaction mixture was stirred for 4 h at RT. The reaction was diluted with EtOAc and washed with 1N aq. HCl (3×), water, brine and saturated aqueous NaHCO$_3$. The organic layer was dried over Na$_2$SO$_4$, filtered, and concentrated. The residue was purified by chromatography (Isco CombiFlash system, using 24 g RediSep silica gel gold column, and 0-20% MeOH/DCM as eluent) to afford compound I-93. MS (ESI) [M+H]$^+$: m/z 373.

Step 2: 4-Cyano-N-(1-(4-(6-cyclopropylpyridin-3-yl)-3-fluorophenyl)cyclobutyl)benzamide Compound I-93 (76 mg, 0.204 mmol) and 1,1'-bis(di-tert-butylphosphino)ferrocene palladium dichloride (11.96 mg, 0.018 mmol) were dissolved in 1,4-dioxane (2.0 ml) in a 20 mL round bottom flask. Sodium carbonate (0.204 ml, 0.408 mmol) was added and the reaction mixture was evacuated and refilled with nitrogen three times and heated at 80° C. for 4 h. The reaction mixture was cooled down, filtered through a Celite pad and concentrated. The crude material was purified by mass-directed reversed phase chromatography (ACN/water gradient with 0.1% TFA modifier) to afford the title compound. MS (ESI) [M+H]$^+$: m/z 412. $^1$H NMR (499 MHz, DMSO-d6) δ 9.40 (s, 1H), 8.66 (s, 1H), 8.04 (d, J=8.1 Hz, 3H), 7.97 (d, J=8.1 Hz, 2H), 7.56 (t, J=8.2 Hz, 1H), 7.49 (d, J=8.2 Hz, 1H), 7.42 (t, J=9.6 Hz, 2H), 2.61 (dt, J=13.2, 7.7 Hz, 3H), 2.13-1.98 (m, 2H), 1.96-1.82 (m, 2H), 1.09 (d, J=7.5 Hz, 2H), 1.03 (s, 2H).

Example 7: 4-Cyano-N-(1-(4-(6-cyclopropyl-4-methylpyridin-3-yl)-3-fluorophenyl)cyclobutyl)benzamide The title compound was prepared in an analogous manner to Example 6 except 2-cyclopropyl-4-methyl-5-(4,4,5,5-tetramethyl-1,3,2-dioxaborolan-2-yl)pyridine was used. MS (ESI) [M+H]$^+$: m/z 426. $^1$H NMR (499 MHz, DMSO-d6) δ 9.39 (s, 1H), 8.45 (s, 1H), 8.06 (d, J=8.2 Hz, 2H), 7.98 (d, J=8.2 Hz, 2H), 7.49 (s, 1H), 7.44 (t, J=8.7 Hz, 2H), 7.38 (t, J=7.9 Hz, 1H), 2.61 (dq, J=18.1, 11.7, 9.7 Hz, 3H), 2.23 (d, J=9.8 Hz, 3H), 2.12-1.97 (m, 2H), 1.97-1.86 (m, 2H), 1.16 (dd, J=22.9, 5.4 Hz, 2H), 1.09 (s, 2H).

Examples 8-39 were prepared in a similar fashion as Example 6 by using bromo intermediate I-86 and the respective boronates.

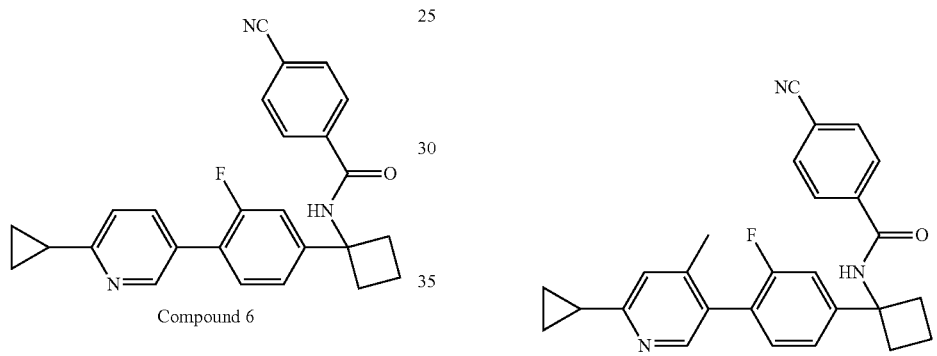

| Ex. # | Structure | Chemical Name | Mass [M + H]+ |
|---|---|---|---|
| 8 | 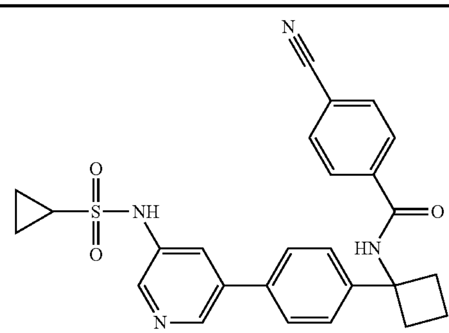 | 4-cyano-N-(1-(4-(5-(cyclopropanesulfonamido)pyridin-3-yl)phenyl)cyclobutyl)benzamide | 473 |

-continued

| Ex. # | Structure | Chemical Name | Mass [M + H]+ |
|---|---|---|---|
| 9 | 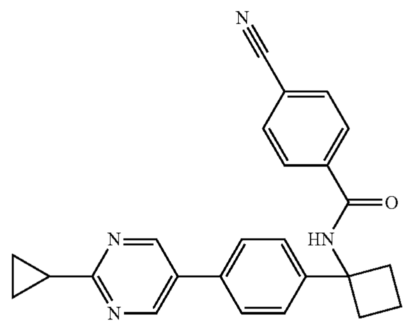 | 4-cyano-N-(1-(4-(2-cyclopropylpyrimidin-5-yl)phenyl)cyclobutyl)benzamide | 394 |
| 10 | 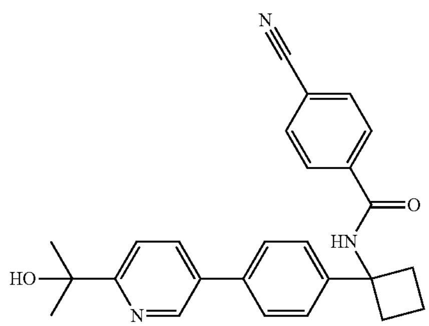 [SMILES: CC(C)(O)c1ccc(-c2ccc(C3(NC(=O)c4ccc(C#N)cc4)CCC3)cc2)cn1] | 4-cyano-N-(1-(4-(6-(2-hydroxypropan-2-yl)pyridin-3-yl)phenyl)cyclobutyl)benzamide | 412 |
| 11 | 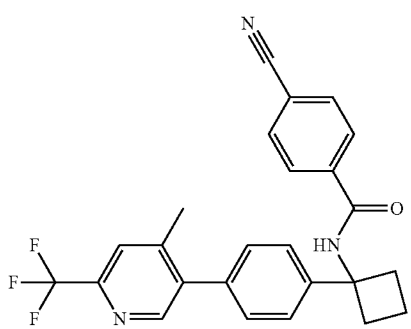 [SMILES: Cc1cc(C(F)(F)F)ncc1-c1ccc(C2(NC(=O)c3ccc(C#N)cc3)CCC2)cc1] | 4-cyano-N-(1-(4-(4-methyl-6-(trifluoromethyl)pyridin-3-yl)phenyl)cyclobutyl)benzamide | 436 |
| 12 | 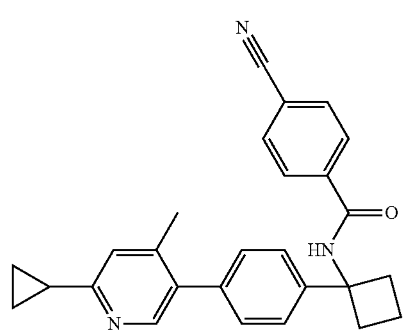 [SMILES: Cc1cc(C2CC2)ncc1-c1ccc(C2(NC(=O)c3ccc(C#N)cc3)CCC2)cc1] | 4-cyano-N-(1-(4-(6-cyclopropyl-4-methylpyridin-3-yl)phenyl)cyclobutyl)benzamide | 408 |

-continued

| Ex. # | Structure | Chemical Name | Mass [M + H]+ |
|---|---|---|---|
| 13 | 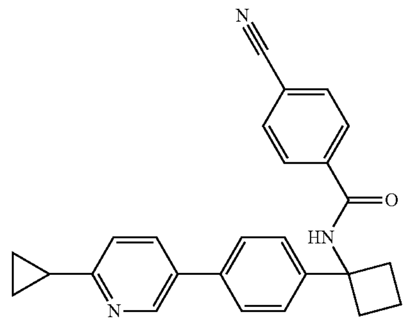 [SMILES: N#Cc1ccc(C(=O)NC2(c3ccc(-c4ccc(C5CC5)nc4)cc3)CCC2)cc1] | 4-cyano-N-(1-(4-(6-cyclopropylpyridin-3-yl)phenyl)cyclobutyl)benzamide | 394 |
| 14 | 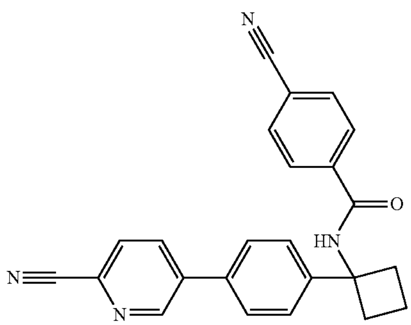 [SMILES: N#Cc1ccc(C(=O)NC2(c3ccc(-c4ccc(C#N)nc4)cc3)CCC2)cc1] | 4-cyano-N-(1-(4-(6-cyanopyridin-3-yl)phenyl)cyclobutyl)benzamide | 378 |
| 15 | 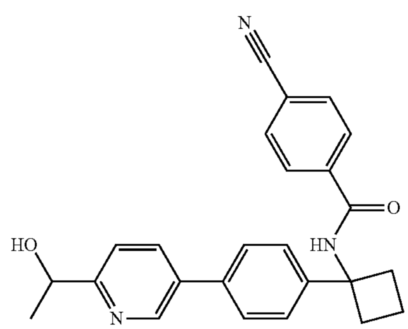 [SMILES: CC(O)c1ccc(-c2ccc(C3(NC(=O)c4ccc(C#N)cc4)CCC3)cc2)cn1] | 4-cyano-N-(1-(4-(6-(1-hydroxyethyl)pyridin-3-yl)phenyl)cyclobutyl)benzamide | 398 |
| 16 | 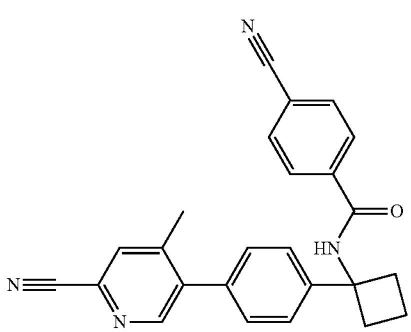 [SMILES: Cc1cc(C#N)ncc1-c1ccc(C2(NC(=O)c3ccc(C#N)cc3)CCC2)cc1] | 4-cyano-N-(1-(4-(6-cyano-4-methylpyridin-3-yl)phenyl)cyclobutyl)benzamide | 393 |

-continued

| Ex. # | Structure | Chemical Name | Mass [M + H]+ |
|---|---|---|---|
| 17 | 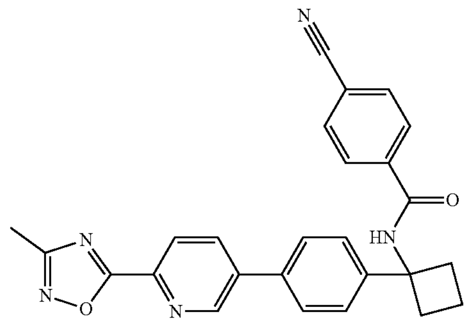 [SMILES: Cc1noc(-c2ccc(-c3ccc(C4(NC(=O)c5ccc(C#N)cc5)CCC4)cc3)cn2)n1] | 4-cyano-N-(1-(4-(6-(3-methyl-1,2,4-oxadiazol-5-yl)pyridin-3-yl)phenyl)cyclobutyl)benzamide | 436 |
| 18 | 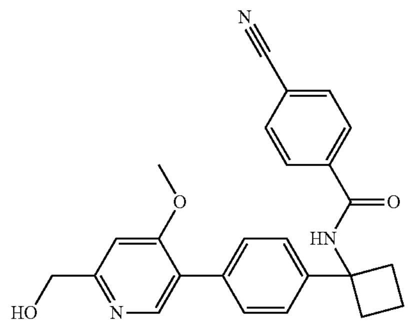 [SMILES: COc1cc(CO)ncc1-c1ccc(C2(NC(=O)c3ccc(C#N)cc3)CCC2)cc1] | 4-cyano-N-(1-(4-(6-(hydroxymethyl)-4-methoxypyridin-3-yl)phenyl)cyclobutyl)benzamide | 414 |
| 19 | 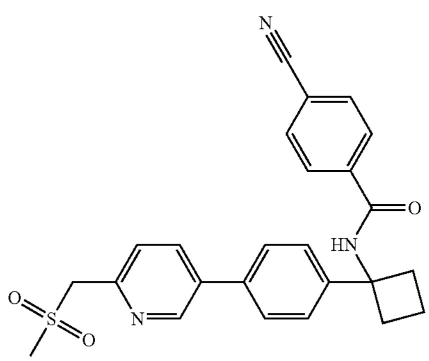 [SMILES: CS(=O)(=O)Cc1ccc(-c2ccc(C3(NC(=O)c4ccc(C#N)cc4)CCC3)cc2)cn1] | 4-cyano-N-(1-(4-(6-((methylsulfonyl)methyl)pyridin-3-yl)phenyl)cyclobutyl)benzamide | 446 |
| 20 | 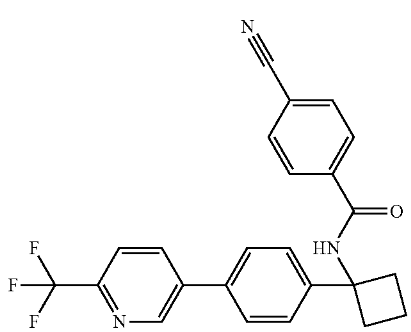 [SMILES: N#Cc1ccc(C(=O)NC2(c3ccc(-c4ccc(C(F)(F)F)nc4)cc3)CCC2)cc1] | 4-cyano-N-(1-(4-(6-(trifluoromethyl)pyridin-3-yl)phenyl)cyclobutyl)benzamide | 422 |

-continued

| Ex. # | Structure | Chemical Name | Mass [M + H]+ |
|---|---|---|---|
| 21 | 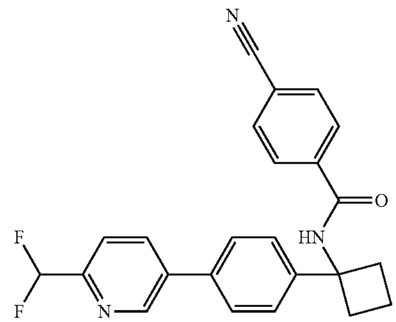 [SMILES: N#Cc1ccc(C(=O)NC2(c3ccc(-c4ccc(C(F)F)nc4)cc3)CCC2)cc1] | 4-cyano-N-(1-(4-(6-(difluoromethyl)pyridin-3-yl)phenyl)cyclobutyl)benzamide | 404 |
| 22 | 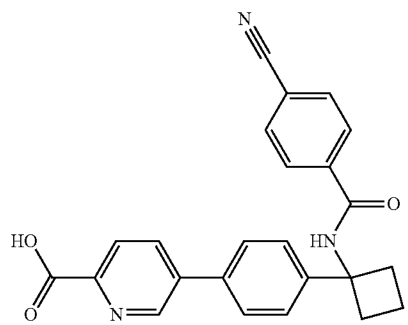 [SMILES: N#Cc1ccc(C(=O)NC2(c3ccc(-c4ccc(C(=O)O)nc4)cc3)CCC2)cc1] | 5-(4-(1-(4-cyanobenzamido)cyclobutyl)phenyl)picolinic acid | 398 |
| 23 | 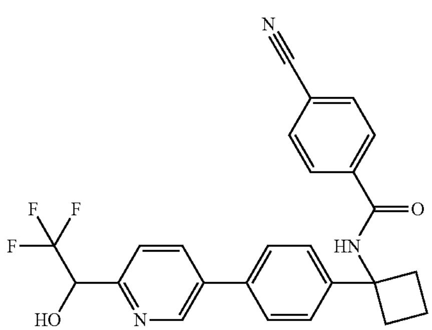 [SMILES: N#Cc1ccc(C(=O)NC2(c3ccc(-c4ccc(C(O)C(F)(F)F)nc4)cc3)CCC2)cc1] | 4-cyano-N-(1-(4-(6-(2,2,2-trifluoro-1-hydroxyethyl)pyridin-3-yl)phenyl)cyclobutyl)benzamide | 452 |
| 24 | 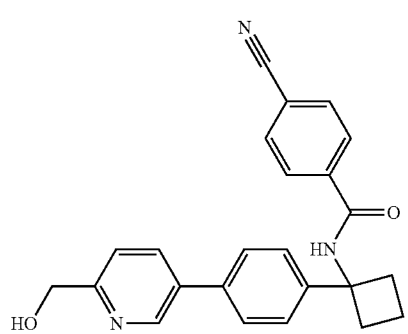 [SMILES: N#Cc1ccc(C(=O)NC2(c3ccc(-c4ccc(CO)nc4)cc3)CCC2)cc1] | 4-cyano-N-(1-(4-(6-(hydroxymethyl)pyridin-3-yl)phenyl)cyclobutyl)benzamide | 384 |

| Ex. # | Structure | Chemical Name | Mass [M + H]+ |
|---|---|---|---|
| 25 | 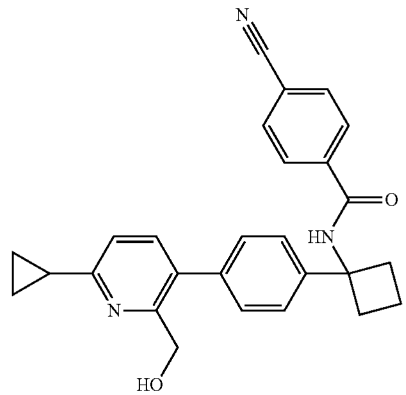 [SMILES: N#Cc1ccc(C(=O)NC2(c3ccc(-c4ccc(C5CC5)nc4CO)cc3)CCC2)cc1] | 4-cyano-N-(1-(4-(6-cyclopropyl-2-(hydroxymethyl)pyridin-3-yl)phenyl)cyclobutyl)benzamide | 424 |
| 26 | 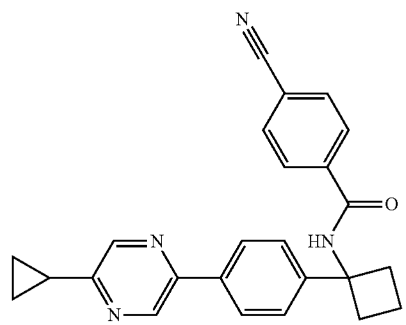 | 4-cyano-N-(1-(4-(5-cyclopropylpyrazin-2-yl)phenyl)cyclobutyl)benzamide | 395 |
| 27 | 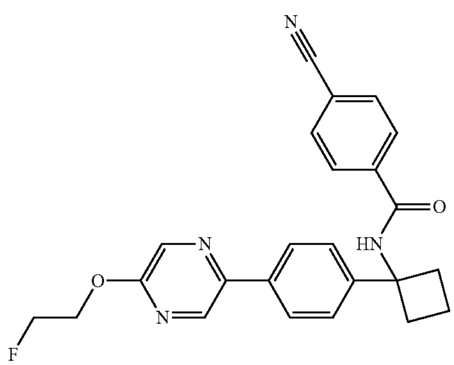 [SMILES: N#Cc1ccc(C(=O)NC2(c3ccc(-c4cnc(OCCF)cn4)cc3)CCC2)cc1] | 4-cyano-N-(1-(4-(5-(2-fluoroethoxy)pyrazin-2-yl)phenyl)cyclobutyl)benzamide | 417 |
| 28 | 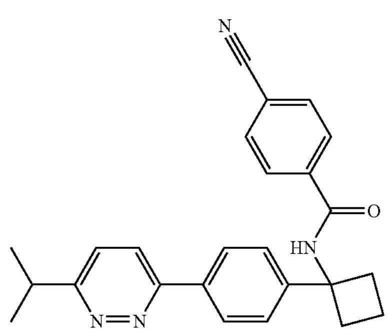 [SMILES: CC(C)c1ccc(-c2ccc(C3(NC(=O)c4ccc(C#N)cc4)CCC3)cc2)nn1] | 4-cyano-N-(1-(4-(6-isopropylpyridazin-3-yl)phenyl)cyclobutyl)benzamide | 397 |

-continued

| Ex. # | Structure | Chemical Name | Mass [M + H]+ |
|---|---|---|---|
| 29 | 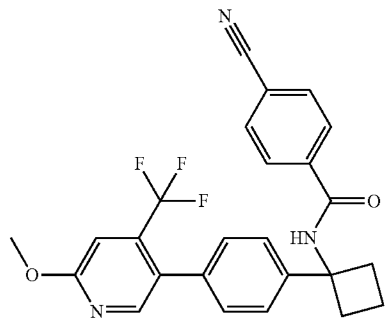 [SMILES: COc1cc(C(F)(F)F)c(-c2ccc(C3(NC(=O)c4ccc(C#N)cc4)CCC3)cc2)cn1] | 4-cyano-N-(1-(4-(6-methoxy-4-(trifluoromethyl)pyridin-3-yl)phenyl)cyclobutyl)benzamide | 452 |
| 30 | 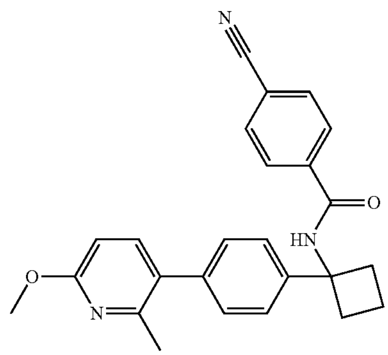 [SMILES: COc1ccc(-c2ccc(C3(NC(=O)c4ccc(C#N)cc4)CCC3)cc2)c(C)n1] | 4-cyano-N-(1-(4-(6-methoxy-2-methylpyridin-3-yl)phenyl)cyclobutyl)benzamide | 398 |
| 31 | 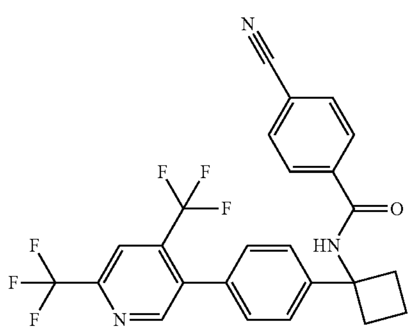 [SMILES: N#Cc1ccc(C(=O)NC2(c3ccc(-c4cnc(C(F)(F)F)cc4C(F)(F)F)cc3)CCC2)cc1] | N-(1-(4-(4,6-bis(trifluoromethyl)pyridin-3-yl)phenyl)cyclobutyl)-4-cyanobenzamide | 490 |
| 32 | 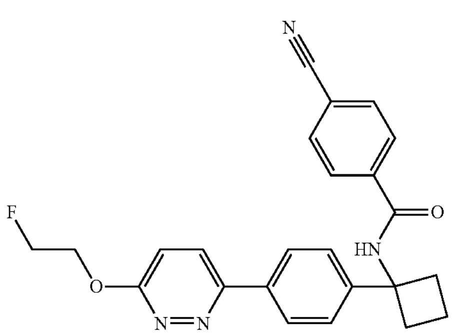 [SMILES: N#Cc1ccc(C(=O)NC2(c3ccc(-c4ccc(OCCF)nn4)cc3)CCC2)cc1] | 4-cyano-N-(1-(4-(6-(2-fluoroethoxy)pyridazin-3-yl)phenyl)cyclobutyl)benzamide | 417 |

| Ex. # | Structure | Chemical Name | Mass [M + H]+ |
|---|---|---|---|
| 33 | 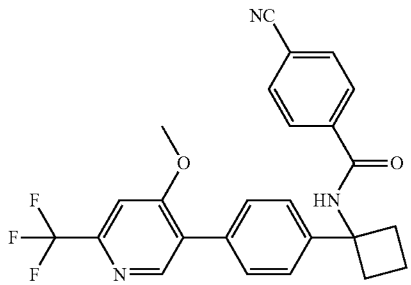 [SMILES: COc1cc(C(F)(F)F)ncc1-c1ccc(C2(NC(=O)c3ccc(C#N)cc3)CCC2)cc1] | 4-cyano-N-(1-(4-(4-methoxy-6-(trifluoromethyl)pyridin-3-yl)phenyl)cyclobutyl)benzamide | 452 |
| 34 | 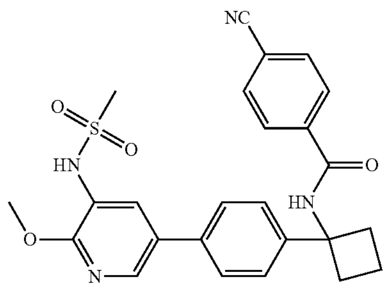 [SMILES: COc1ncc(-c2ccc(C3(NC(=O)c4ccc(C#N)cc4)CCC3)cc2)cc1NS(C)(=O)=O] | cyano-N-(1-(4-(6-methoxy-5-(methylsulfonamido)pyridin-3-yl)phenyl)cyclobutyl)benzamide | 477 |
| 35 | 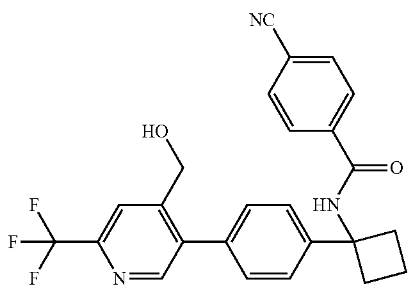 [SMILES: N#Cc1ccc(C(=O)NC2(c3ccc(-c4cnc(C(F)(F)F)cc4CO)cc3)CCC2)cc1] | 4-cyano-N-(1-(4-(4-(hydroxymethyl)-6-(trifluoromethyl)pyridin-3-yl)phenyl)cyclobutyl)benzamide | 452 |
| 36 | 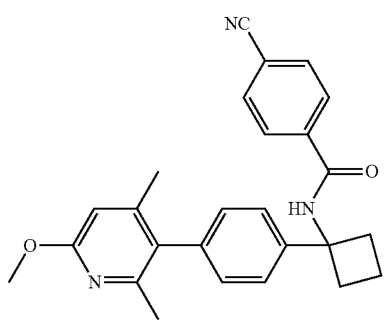 [SMILES: COc1cc(C)c(-c2ccc(C3(NC(=O)c4ccc(C#N)cc4)CCC3)cc2)c(C)n1] | 4-cyano-N-(1-(4-(6-methoxy-2,4-dimethylpyridin-3-yl)phenyl)cyclobutyl)benzamide | 412 |
| 37 | 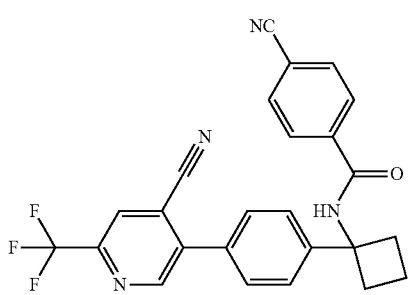 [SMILES: N#Cc1ccc(C(=O)NC2(c3ccc(-c4cnc(C(F)(F)F)cc4C#N)cc3)CCC2)cc1] | 4-cyano-N-(1-(4-(4-cyano-6-(trifluoromethyl)pyridin-3-yl)phenyl)cyclobutyl)benzamide | 447 |

| Ex. # | Structure | Chemical Name | Mass [M + H]+ |
|---|---|---|---|
| 38 | 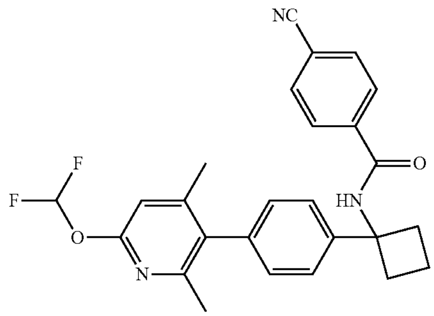 [SMILES: Cc1cc(OC(F)F)nc(C)c1-c1ccc(C2(NC(=O)c3ccc(C#N)cc3)CCC2)cc1] | 4-cyano-N-(1-(4-(6-(difluoromethoxy)-2,4-dimethylpyridin-3-yl)phenyl)cyclobutyl)benzamide | 448 |
| 39 | 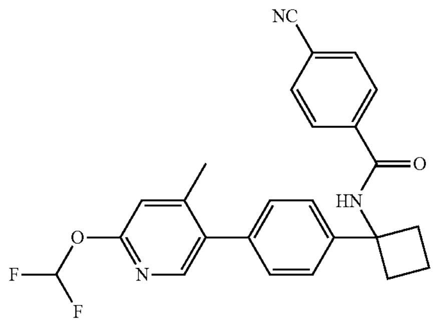 [SMILES: Cc1cc(OC(F)F)ncc1-c1ccc(C2(NC(=O)c3ccc(C#N)cc3)CCC2)cc1] | 4-cyano-N-(1-(4-(6-(difluoromethoxy)-4-methylpyridin-3-yl)phenyl)cyclobutyl)benzamide | 434 |

Examples 40-41 were prepared by the following scheme:

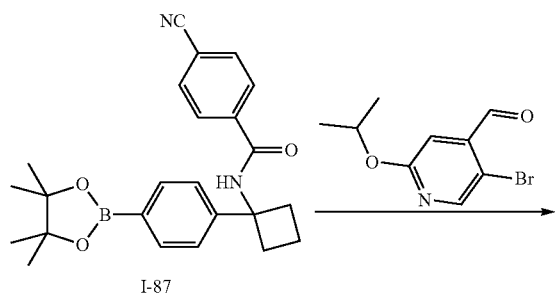

I-87

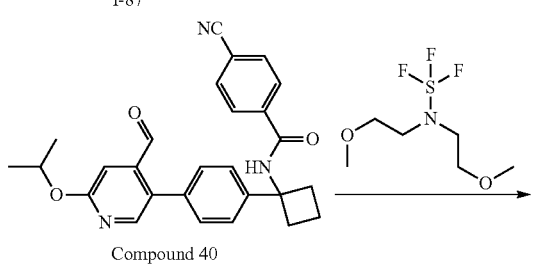

Compound 40

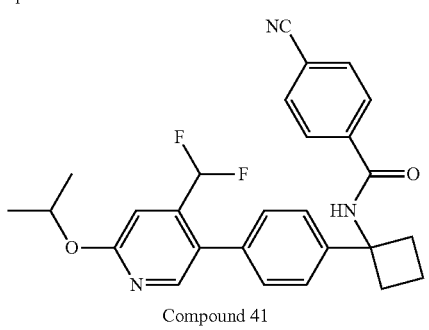

Compound 41

Example 40: 4-Cyano-N-(1-(4-(4-formyl-6-isopropoxypyridin-3-yl)phenyl)cyclobutyl)benzamide To a 25-mL flask containing 5-bromo-2-isopropoxyisonicotinaldehyde (152 mg, 0.621 mmol), 4-cyano-N-(1-(4-(4,4,5,5-tetramethyl-1,3,2-dioxaborolan-2-yl)phenyl)cyclobutyl)benzamide (200.0 mg, 0.497 mmol), tetrakis(triphenylphosphine)palladium(0) (57.4 mg, 0.050 mmol) and $K_2CO_3$ (206 mg, 1.491 mmol) was added 1,4-dioxane (8.0 ml) and water (2.000 ml). The reaction mixture was evacuated and refilled with nitrogen three times and the mixture was heated under nitrogen at 90° C. for 24 h. The solvents were removed under vacuum. The resulting residue was suspended in EtOAc/DCM, filtered through a Celite pad which was washed with EtOAc/DCM. The combined filtrates were concentrated to afford the title compound. MS (ESI) [M+H]+: m/z 440.

Example 41: 4-Cyano-N-(1-(4-(4-(difluoromethyl)-6-isopropoxypyridin-3-yl)phenyl)cyclobutyl)benzamide To a stirred solution of 4-cyano-N-(1-(4-(4-formyl-6-isopropoxypyridin-3-yl)phenyl)cyclobutyl)benzamide (65 mg, 0.148 mmol) in DCM (1.5 ml) at 0° C. was added dropwise bis(2-methoxyethyl)aminosulfur trifluoride (0.104 ml, 0.562 mmol). The reaction mixture was stirred at 0° C. for 2 h, quenched with sat. aq. sodium bicarbonate and extracted with $CH_2Cl_2$ (2×). The combined organics were washed with brine, dried over anhydrous sodium sulfate and concentrated under reduced pressure. The crude material was purified by mass-directed reversed phase chromatography (ACN/water gradient with 0.1% TFA modifier) to afford the title compound. MS (ESI) [M+H]+: m/z 462. $^1$H NMR (499 MHz, DMSO-d6) δ 9.34 (s, 1H), 8.20 (s, 1H), 8.05 (d, J=8.2 Hz, 2H), 7.97 (d, J=8.2 Hz, 2H), 7.58 (d, J=8.1 Hz, 2H), 7.36 (d, J=8.1 Hz, 2H), 6.99 (d, J=8.3 Hz, 1H), 5.32 (dd, J=12.2, 6.1 Hz, 1H), 2.62 (dt, J=24.6, 6.8 Hz, 2H), 2.15-1.82 (m, 2H), 1.34 (s, 3H), 1.32 (s, 3H), 1.25 (dd, J=16.6, 5.9 Hz, 2H).

Example 42: 4-Cyano-N-(1-(6'-cyclopropyl-4'-methyl-[3,3'-bipyridin]-6-yl)cyclobutyl)benzamide

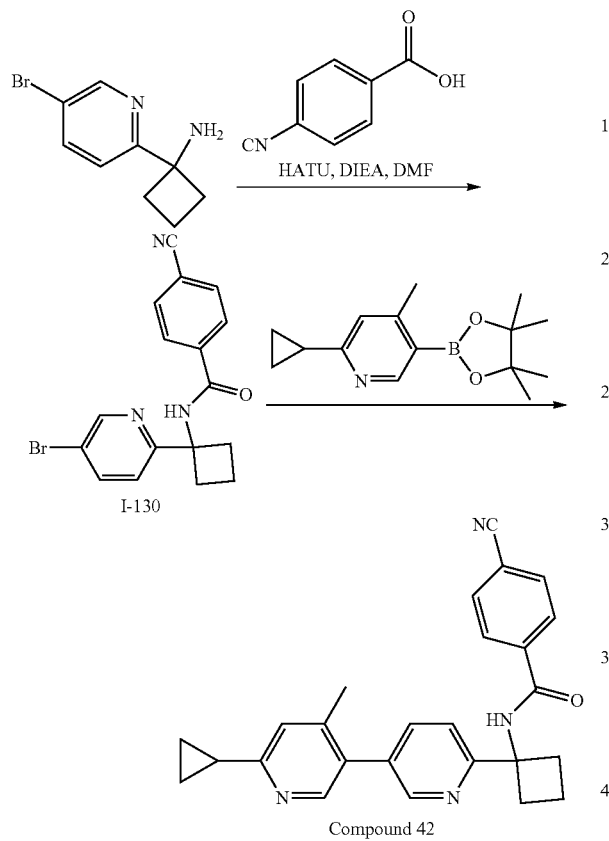

Compound 42

Step 1: Synthesis of N-(1-(5-bromopyridin-2-yl)cyclobutyl)-4-cyanobenzamide (I-130)

To a 40 mL vial charged with 4-isocyanobenzoic acid (324 mg, 2.202 mmol) in DMF (5 ml) was added with stirring HATU (1005 mg, 2.64 mmol) and the reaction was stirred for a few minutes. 1-(5-Bromopyridin-2-yl)cyclobutanamine (500.0 mg, 2.202 mmol) was added followed by DIEA (1.154 ml, 6.60 mmol), and the reaction mixture was stirred for 12 h at RT. The reaction was diluted with EtOAc and washed with 1N aq. HCl (3×), water (2×), brine and sat. aq. NaHCO₃. The organic extracts were then dried over Na₂SO₄, filtered, and concentrated. The residue was purified by chromatography (Isco CombiFlash system, using 48 g RediSep silica gel gold column, 0-20% MeOH/DCM as eluent) to afford compound I-130. MS (ESI) [M+H]⁺: m/z 356.

Step 2: 4-Cyano-N-(1-(6'-cyclopropyl-4'-methyl-[3,3'-bipyridin]-6-yl)cyclobutyl)benzamide 2-Cyclopropyl-4-methyl-5-(4,4,5,5-tetramethyl-1,3,2-dioxaborolan-2-yl)pyridine (43.7 mg, 0.168 mmol), compound I-130 (60.0 mg, 0.168 mmol) and 1,1'-bis(di-tert-butylphosphino)ferrocene palladium dichloride (9.88 mg, 0.015 mmol) were dissolved in 1,4-dioxane (2.0 ml) in a 20 mL round bottom flask, and sodium carbonate (0.168 ml, 0.337 mmol) was added. The reaction mixture was subjected to the standard Suzuki coupling conditions and the crude product was purified by mass-directed reverse phase chromatography (ACN/water gradient with 0.1% TFA modifier) to afford the title compound. MS (ESI) [M+H]⁺: m/z 409. ¹H NMR (499 MHz, DMSO-d6) δ 9.47 (s, 1H), 8.68 (s, 1H), 8.53 (s, 1H), 8.09 (t, J=9.2 Hz, 2H), 8.03-7.96 (m, 2H), 7.90-7.84 (m, 1H), 7.53 (d, J=5.9 Hz, 2H), 2.85-2.71 (m, 2H), 2.58 (q, J=9.2 Hz, 2H), 2.38 (s, 3H), 2.34-2.20 (m, 1H), 2.05 (ddd, J=23.6, 12.6, 5.4 Hz, 2H), 1.26-1.19 (m, 2H), 1.13 (s, 2H).

Example 43: 3-Cyano-N-(1-(6'-(difluoromethoxy)-4'-methyl-[3,3'-bipyridin]-6-yl)cyclobutyl)bicyclo[1.1.1]-pentane-1-carboxamide

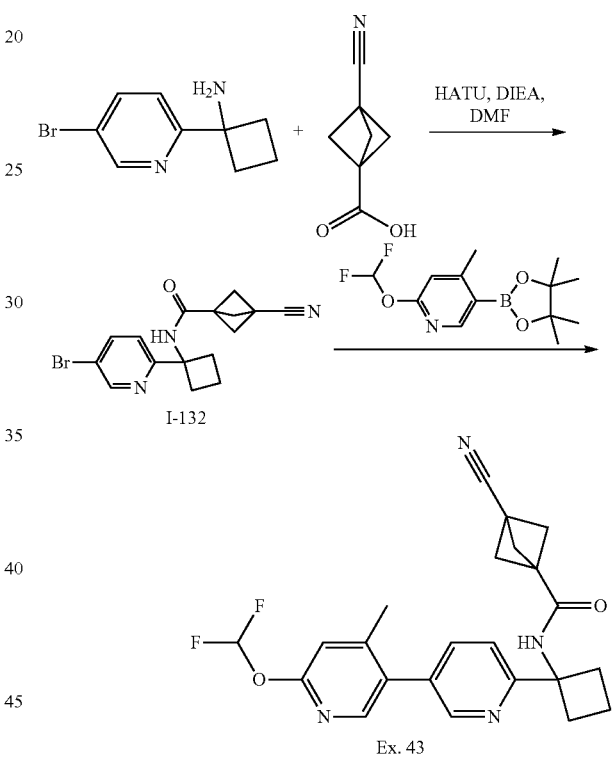

Ex. 43

Step 1: N-(1-(5-bromopyridin-2-yl)cyclobutyl)-3-cyanobicyclo[1.1.1]pentane-1-carboxamide (I-132)

N-(1-(5-bromopyridin-2-yl)cyclobutyl)-3-cyanobicyclo[1.1.1]pentane-1-carboxamide (I-132) was prepared in a manner analogous to the synthesis of intermediate I-130 except 3-cyanobicyclo[1.1.1]pentane-1-carboxylic acid was used. MS (ESI) [M+H]⁺: m/z 346.

Step 2: 3-cyano-N-(1-(6'-(difluoromethoxy)-4'-methyl-[3,3'-bipyridin]-6-yl)cyclobutyl)bicyclo[1.1.1]pentane-1-carboxamide The title compound was prepared with intermediate I-132 and 2-(difluoromethoxy)-4-methyl-5-(4,4,5,5-tetramethyl-1,3,2-dioxaborolan-2-yl)pyridine under the standard Suzuki coupling conditions. MS (ESI) [M+H]⁺: m/z 425. ¹H NMR (499 MHz, DMSO-d6) δ 8.69 (s, 1H), 8.60 (s, 1H), 8.13 (s, 1H), 7.91-7.81 (m, 1H), 7.74 (s, 1H), 7.34 (d, J=8.2 Hz, 1H), 7.12 (s, 1H), 2.66 (dt, J=15.2, 8.8 Hz, 2H), 2.48 (s, 4H), 2.40 (dd, J=18.8, 9.1 Hz, 2H), 2.30 (s, 3H), 2.08-1.90 (m, 4H).

Example 44: 3-Cyano-N-(1-(6'-cyclopropyl-4'-methyl-[3,3'-bipyridin]-6-yl)cyclobutyl)bicyclo[1.1.1]pentane-1-carboxamide

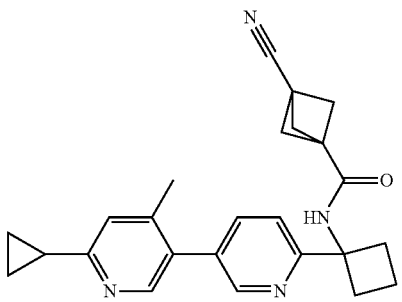 [SMILES: Cc1cc(C2CC2)ncc1-c1ccc(C2(NC(=O)C34CC(C#N)(C3)C4)CCC2)nc1]

This compound was prepared in a similar fashion as Example 43 except 2-cyclopropyl-4-methyl-5-(4,4,5,5-tetramethyl-1,3,2-dioxaborolan-2-yl)pyridine was used. MS (ESI) [M+H]⁺: m/z 399. ¹H NMR (499 MHz, DMSO-d6) δ 8.71 (s, 1H), 8.64 (s, 1H), 8.51 (s, 1H), 7.96-7.75 (m, 1H), 7.52 (s, 1H), 7.35 (d, J=8.2 Hz, 1H), 2.65 (dt, J=15.3, 8.9 Hz, 2H), 2.48 (s, 3H), 2.44-2.39 (m, 2H), 2.37 (s, 2H), 2.25 (dd, J=10.3, 5.6 Hz, 2H), 1.97 (dd, J=14.6, 7.3 Hz, 4H), 1.26-1.18 (m, 2H), 1.12 (s, 3H).

Example 45: 4-Fluoro-N-(3-(4-(4-(hydroxymethyl)-6-(trifluoromethyl)pyridin-3-yl)phenyl)oxetan-3-yl)benzamide

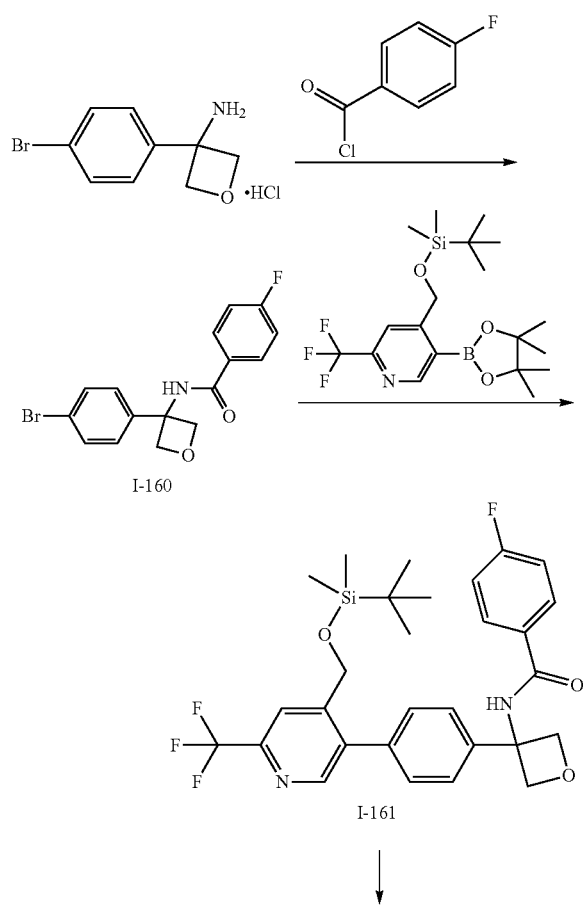

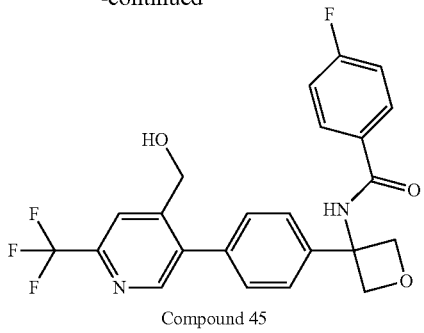

Compound 45

Step 1: N-(3-(4-bromophenyl)oxetan-3-yl)-4-fluorobenzamide (I-160)

To a vial equipped with a stir bar was added commercially available 3-(4-bromophenyl)oxetan-3-amine hydrochloride (300.00 mg, 1.134 mmol), DCM (2.00 ml) and DIEA (0.990 ml, 5.67 mmol). To this stirred solution at 0° C. was then added 4-fluorobenzoyl chloride (0.161 ml, 1.361 mmol) and the reaction mixture was allowed to stir for 2 h. The reaction mixture was partitioned into excess DCM, washed with sat. NaHCO₃, and the organic layers was separated, washed with water and brine, dried over MgSO₄, filtered and the filtrates were concentrated under reduced pressure. The oil obtained was purified on a silica gel column using (0-60%) Hex-3:1 EtOAc-Ethanol to give compound I-160 as a solid. MS (ESI) [M+H]⁺: m/z 352.

Step 2: N-(3-(4-(4-(((tert-butyldimethylsilyl)oxy)methyl)-6-(trifluoromethyl)pyridin-3-yl)phenyl)oxetan-3-yl)-4-fluorobenzamide (I-161)

To a vial were added 4-(((tert-butyldimethylsilyl)oxy)methyl)-5-(4,4,5,5-tetramethyl-1,3,2-dioxaborolan-2-yl)-2-(trifluoromethyl)pyridine (179 mg, 0.428 mmol), compound I-160 (100 mg, 0.286 mmol), 1,1'-bis(di-tert-butylphosphino)palladium dichloride (27.9 mg, 0.043 mmol), and 2 M aq. solution of sodium carbonate (286 µl, 0.571 mmol) and 1,4-dioxane (1904 µl). The vial was evacuated and purged with nitrogen thrice and the mixture was heated under nitrogen and then subjected to microwave irradiation at 110° C. for 40 min. The reaction mixture was cooled, diluted with water, and extracted with EtOAc. The organic layers were separated, washed with brine, dried over MgSO₄, and concentrated. The residue was purified on a silica gel column using 0-70% Hex-EtOAc/Ethanol (3:1 mixture) to give compound I-161 as a solid. MS (ESI) [M+H]⁺: m/z 561.

Step 3: 4-Fluoro-N-(3-(4-(4-(hydroxymethyl)-6-(trifluoromethyl)pyridin-3-yl)phenyl)oxetan-3-yl)benzamide To a stirred solution of compound I-161 (155.40 mg, 0.277 mmol) in THF (0.5 ml) in a vial, was added TBAF (1.109 ml, 1.109 mmol) and the reaction mixture was allowed to stir for 2 h. The reaction was diluted with sat. NaHCO₃ solution and excess EtOAc. The organic layer was separated, washed with water and brine, dried over MgSO₄, filtered and the solvents were removed under reduced pressure. The oil obtained was purified on a silica gel column using (0-60%) Hex-3:1 EtOAc-Ethanol mixture to give the title compound as a solid. MS ESI [M+H]⁺: m/z 447. ¹H NMR (600 MHz, DMSO-d6) δ 9.61 (s, 1H), 8.62 (s, 1H), 8.18-7.94 (m, 3H), 7.69 (d, J=8.4 Hz, 2H), 7.52 (d, J=8.4 Hz, 2H), 7.37 (t, J=8.8 Hz, 2H), 5.67 (t, J=5.5 Hz, 1H), 5.06 (d, J=7.0 Hz, 2H), 4.84 (s, 1H), 4.57 (d, J=5.4 Hz, 2H).

Example 46: 4-chloro-N-(1-(4-(4-(hydroxymethyl)-6-(trifluoromethyl)pyridin-3-yl)phenyl)cyclopropyl)benzamide

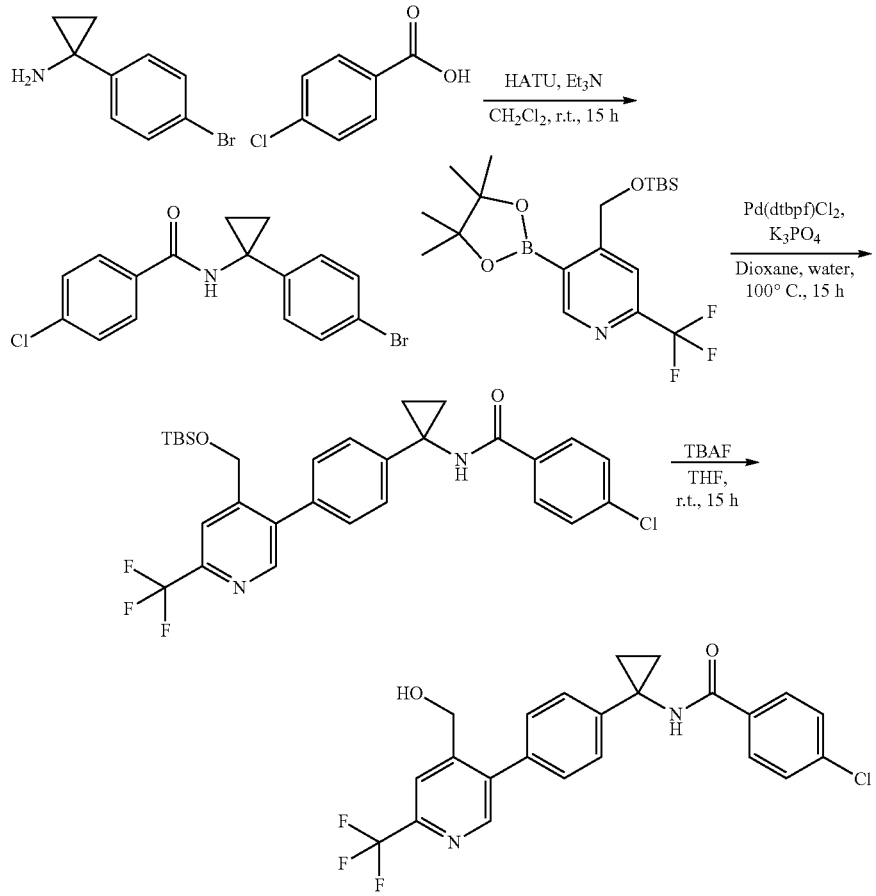

Step 1: N-(1-(4-bromophenyl)cyclopropyl)-4-chlorobenzamide

To a stirred solution of 1-(4-bromophenyl)cyclopropanamine (200 mg, 0.943 mmol) in CH$_2$Cl$_2$ (10 mL) were added 4-chlorobenzoic acid (221 mg, 1.415 mmol), TEA (0.4 mL, 2.87 mmol) and HATU (538 mg, 1.415 mmol) at RT and the reaction was stirred at RT for 15 h. The solvent was concentrated and the residue was diluted with water (20 mL) and extracted with EtOAc (30 mL×2). The organic layers were collected, washed with brine (20 mL), dried over Na$_2$SO$_4$, filtered, and the filtrate was concentrated in vacuo. The residue was first purified by silica gel chromatography followed by additional purification using reversed phase HPLC on a GILSON 281 instrument fitted with a Waters Xbridge Prep OBD C18 column (100×19 mm×5 um) using water (0.225% formic acid)-ACN as eluents. The title compound was obtained as a solid after concentration of the desired fractions. MS (ESI) m/z: 349.9 [M+H$^+$].

Step 2: N-(1-(4-(4-(((tert-butyldimethylsilyl)oxy)methyl)-6-(trifluoromethyl)pyridin-3-yl)phenyl)cyclopropyl)-4-chlorobenzamide To a stirred solution of N-(1-(4-bromophenyl)cyclopropyl)-4-chlorobenzamide (50 mg, 0.143 mmol) in 1,4-dioxane (2.5 mL) and water (0.5 mL) were added Pd(dppf)Cl$_2$ (10 mg, 0.014 mmol) and K$_3$PO$_4$ (91 mg, 0.428 mmol) at RT and the reaction was heated to 100° C. with stirring for 5 h. After cooled to RT, the solvent was concentrated, and the residue was diluted with water (20 mL) and extracted by EtOAc (30 mL×2). The organic layers were collected, washed with brine (20 mL), dried over Na$_2$SO$_4$, filtered, and the filtrate was concentrated in vacuo. The residue was purified by silica gel chromatography to afford the title compound as a solid. $^1$H NMR (400 MHz, CDCl$_3$) δ 8.5 (s, 1 H), 8.0 (s, 1 H), 7.7-7.8 (m, 2 H), 7.4 (d, 2 H), 7.4 (d, 2 H), 7.2 (d, 2 H), 6.9 (br s, 1 H), 4.7 (s, 2 H), 1.3 (br s, 2 H), 0.9 (s, 9 H), 0.8-0.9 (m, 2 H), 0.0 (s, 6 H).

Step 3: 4-chloro-N-(1-(4-(4-(hydroxymethyl)-6-(trifluoromethyl)pyridin-3-yl)phenyl)cyclopropyl)benzamide To a stirred solution of N-(1-(4-(4-(((tert-butyldimethylsilyl)oxy)methyl)-6-(trifluoromethyl)pyridin-3-yl)phenyl)cyclopropyl)-4-chlorobenzamide (106 mg, 0.189 mmol) in THF (10 mL) was added TBAF (0.4 mL, 0.400 mmol) at RT and the mixture was stirred at RT for 15 h. The solvent was removed in vacuo, the residue was quenched with water (30 mL) and extracted with EtOAc (30 mL×2). The organic layers were collected, washed with brine (20 mL), dried over Na$_2$SO$_4$, filtered, and the filtrate was concentrated in vacuo. The residue was purified by reversed phase HPLC on a GILSON 281 instrument fitted with a Waters Xbridge Prep OBD C18 column (100×19 mm×5 um) using water (0.225% formic acid)-ACN as mobile phases to afford the title compound as a solid. $^1$H NMR (400 MHz, CDCl$_3$) δ 8.54 (s, 1 H), 8.02 (s, 1 H), 7.75-7.79 (m, 2 H), 7.42-7.46 (m, 2 H), 7.37-7.40 (m, 2 H), 7.23-7.26 (m, 2 H), 4.72 (s, 2 H), 1.46 (s, 4 H). MS (ESI) m/z: 447.1 [M+H$^+$].

Example 47: N-(1-(4-(6-cyclopropoxy-4-(2-hydroxypropan-2-yl)pyridin-3-yl)phenyl)cyclopropyl)-4-fluorobenzamide

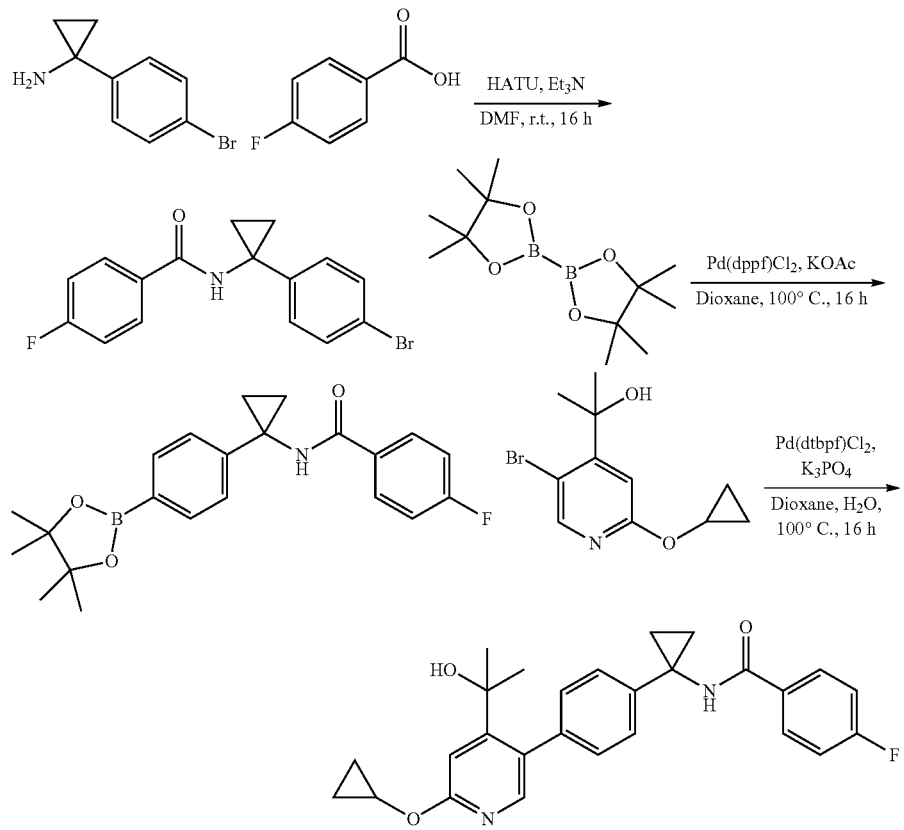

Step 1: N-(1-(4-bromophenyl)cyclopropyl)-4-fluorobenzamide

To a stirred solution of 4-fluorobenzoic acid (290 mg, 2.070 mmol) in DMF (8 mL) were added HATU (905 mg, 2.380 mmol), 1-(4-bromophenyl)cyclopropanamine (505 mg, 2.380 mmol) and TEA (0.87 mL, 6.24 mmol) at RT and the mixture was stirred RT for 16 h. Then the mixture was diluted with water (50 mL), extracted with EtOAc (30 mL×3), and the organic layers were collected, washed with brine, dried over $Na_2SO_4$, and filtered. After filtration, the filtrate was concentrated in vacuo. The residue was purified by flash silica gel chromatography to afford the title compound as a solid. MS (ESI) m/z: 333.9 [M+H$^+$].

Step 2: 4-fluoro-N-(1-(4-(4,4,5,5-tetramethyl-1,3,2-dioxaborolan-2-yl)phenyl)cyclopropyl)benzamide To a stirred solution of N-(1-(4-bromophenyl)cyclopropyl)-4-fluorobenzamide (280 mg, 0.838 mmol) in 1,4-dioxane (10 mL) were added 4,4,4',4',5,5,5',5'-octamethyl-2,2'-bi(1,3,2-dioxaborolane) (255 mg, 1.005 mmol), potassium acetate (247 mg, 2.51 mmol) and Pd(dppf)Cl$_2$ (62 mg, 0.085 mmol) at RT and the reaction was subjected to the typical Suzuki coupling conditions. The crude product was purified by flash silica gel chromatography to afford the title compound as a solid. MS (ESI) m/z: 382.1 [M+H$^+$].

Step 3: N-(1-(4-(6-cyclopropoxy-4-(2-hydroxypropan-2-yl)pyridin-3-yl)phenyl)cyclopropyl)-4-fluorobenzamide To a solution of 2-(5-bromo-2-cyclopropoxypyridin-4-yl)propan-2-ol (40 mg, 0.147 mmol) and 4-fluoro-N-(1-(4-(4,4,5,5-tetramethyl-1,3,2-dioxaborolan-2-yl)phenyl)cyclopropyl)benzamide (56 mg, 0.147 mmol) in dioxane (5 mL) and water (1 mL) were added Pd(dtbpf)Cl$_2$ (9 mg, 0.014 mmol) and K$_3$PO$_4$ (94 mg, 0.441 mmol) at RT and the reaction mixture was stirred at 100° C. under nitrogen for 16 h. Then the mixture was cooled to RT, filtered through a pad of Celite, and the filtrate was concentrated under reduced pressure to give a residue, which was purified by reversed phase HPLC on a GILSON 281 instrument fitted with a Waters XSELECT C18 column (150×30 mm×5 um) using water (0.1% TFA) and ACN as eluents followed by freeze drying to afford the title compound as a solid. $^1$H NMR (400 MHz, CD$_3$OD) δ 7.93 (dd, 2 H), 7.78 (s, 1 H), 7.63 (br s, 1 H), 7.28-7.34 (m, 2 H), 7.15-7.24 (m, 4 H), 4.20 (br s, 1 H), 1.40 (s, 4 H), 1.31 (s, 6 H), 0.89 (br d, 2 H), 0.82 (br s, 2 H). MS (ESI) m/z: 447.2 [M+H$^+$].

Example 48: N-(1-(4-(6-cyclopropoxy-4-(hydroxymethyl)pyridin-3-yl)phenyl)cyclopropyl)-4-fluorobenzamide

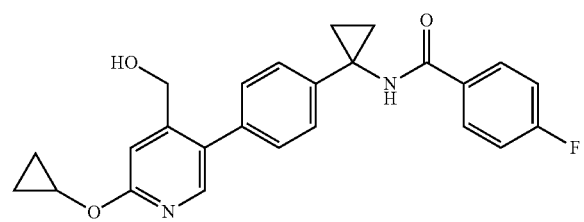 [SMILES: O=C(NC1(c2ccc(-c3cnc(OC4CC4)cc3CO)cc2)CC1)c1ccc(F)cc1]

The title compound was prepared using intermediate 4-fluoro-N-(1-(4-(4,4,5,5-tetramethyl-1,3,2-dioxaborolan-2-yl)phenyl)cyclopropyl)benzamide and 5-bromo-2-cyclopropoxypyridin-4-yl)methanol in a similar fashion as Example 47. $^1$H NMR (400 MHz, CD$_3$OD) δ 8.00 (s, 1 H), 7.93 (dd, 2 H), 7.55 (br s, 1 H), 7.34-7.40 (m, 2 H), 7.25-7.30 (m, 2 H), 7.21 (t, 2 H), 4.59 (s, 2 H), 4.26 (br s, 1 H), 1.41 (s, 4 H), 0.93 (br d, 2 H), 0.87 (br s, 2 H). MS (ESI) m/z: 419.2 [M+H$^+$].

Example 49: 4-fluoro-N-(1-(4-(4-(hydroxymethyl)-6-isopropoxypyridin-3-yl)phenyl)cyclopropyl)benzamide

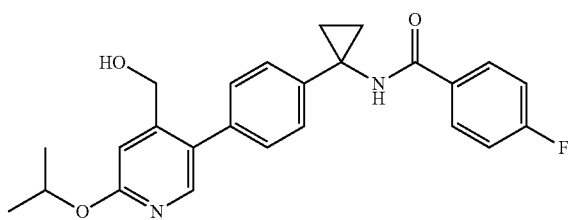 [SMILES: CC(C)Oc1cc(CO)c(-c2ccc(C3(NC(=O)c4ccc(F)cc4)CC3)cc2)cn1]

Step 1: 5-bromo-2-isopropoxyisonicotinaldehyde

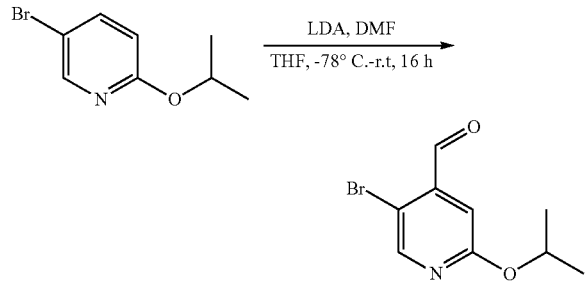

To a solution of 5-bromo-2-isopropoxypyridine (500 mg, 2.314 mmol) in THF (8 mL) was added LDA (1.4 mL, 2.80 mmol) (2M in THF) at −78° C. and the mixture was stirred at −78° C. for 1 h. Then DMF (300 mg, 4.10 mmol) was added at −78° C. and the reaction was gradually warmed to RT and stirred for 16 h. The mixture was quenched with water (10 mL), extracted with EtOAc (10 mL×2), the organic layers were collected, washed with brine, dried over Na$_2$SO$_4$, and filtered. After filtration, the filtrate was concentrated in vacuo. The residue was purified by flash silica gel chromatography to afford the title compound. $^1$H NMR (400 MHz, CD$_3$OD) δ 8.05-8.22 (m, 1 H), 6.94 (s, 1 H), 5.19 (spt, 1 H), 1.30 (d, 6 H).

Step 2: (5-bromo-2-isopropoxypyridin-4-yl)methanol

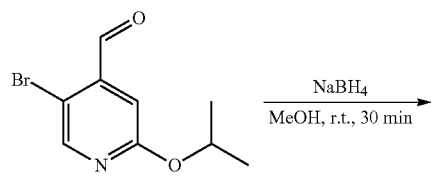

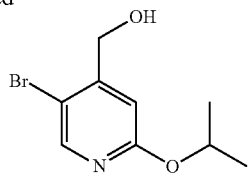

To a solution of 5-bromo-2-isopropoxyisonicotinaldehyde (120 mg, 0.492 mmol) in MeOH (5 mL) was added NaBH$_4$ (23 mg, 0.608 mmol) at 0° C., and the mixture was stirred at 0° C. for 30 min and quenched with water (10 mL). The MeOH was removed in vacuo and the aq. residue was extracted with EtOAc (10 mL×3). The organic layers were collected, washed with brine, dried over Na$_2$SO$_4$, and filtered. After filtration, the filtrate was concentrated in vacuo to afford the title compound as an oil, which was used directly in the next step without further purification. MS (ESI) m/z: 246.0 [M+H$^+$].

Step 3: 4-fluoro-N-(1-(4-(4-(hydroxymethyl)-6-isopropoxypyridin-3-1)phenyl)cyclopropyl)benzamide The title compound was prepared in a similar fashion to Example 47 using (5-bromo-2-isopropoxypyridin-4-yl)methanol and 4-fluoro-N-(1-(4-(4,4,5,5-tetramethyl-1,3,2-dioxaborolan-2-yl)phenyl)cyclopropyl)benzamide as Suzuki coupling partners and the crude was purified by reversed phase HPLC on a GILSON 281 instrument fitted with a Agela ASB C18 column (150×25 mm×5 um) using water (0.225% formic acid) and ACN. $^1$H NMR (400 MHz, CD$_3$OD) δ 7.97-8.01 (m, 1 H), 7.93 (dd, 2 H), 7.32-7.41 (m, 3 H), 7.25-7.30 (m, 2 H), 7.20 (t, 2 H), 5.22 (dt, 1 H), 4.58 (s, 2 H), 1.43-1.47 (m, 6 H), 1.41 (s, 4 H). MS (ESI) m/z: 421.2 [M+H$^+$].

Example 50: (S)-4-fluoro-N-(1-(4-(4-(1-hydroxyethyl)-6-(trifluoromethyl)pyridin-3-yl)phenyl)cyclopropyl)benzamide

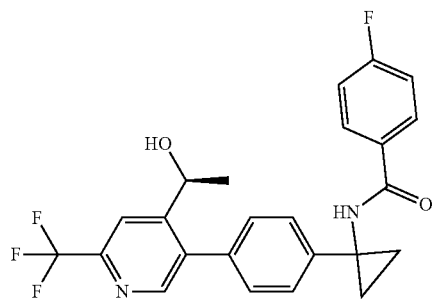

The title compound was prepared in a similar fashion as Example 49 using (S)-1-(5-bromo-2-(trifluoromethyl)pyridin-4-yl)ethanol as the coupling partner. $^1$H NMR (499 MHz, DMSO-d6) δ 9.26 (s, 1H), 8.51 (s, 1H), 8.11-7.92 (m, 3H), 7.41-7.26 (m, 6H), 4.92-4.77 (m, 1H), 1.43-1.30 (m, 4H), 1.24-1.14 (m, 4H). MS (ESI) m/z: 445.1 [M+1]$^+$.

Example 51: (R)-4-fluoro-N-(1-(4-(4-(1-hydroxy-ethyl)-6-(trifluoromethyl)pyridin-3-yl)phenyl)cyclopropyl)benzamide, 2,2,2-trifluoroacetate salt

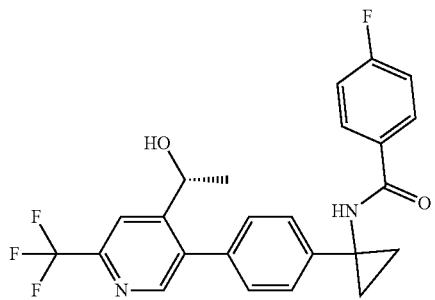 [SMILES: C[C@@H](O)c1cc(C(F)(F)F)ncc1-c1ccc(C2(NC(=O)c3ccc(F)cc3)CC2)cc1]

The title compound was prepared in a similar fashion as Example 49 using (R)-1-(5-bromo-2-(trifluoromethyl)pyridin-4-yl)ethanol the coupling partner. $^1$H NMR (499 MHz, DMSO-d$_6$) δ 9.26 (s, 1H), 8.51 (s, 1H), 8.10-7.93 (m, 3H), 7.43-7.26 (m, 6H), 4.97-4.73 (m, 2H), 1.41-1.31 (m, 4H), 1.23-1.15 (m, 3H). MS (ESI) m/z: 445.1 [M+H]$^+$.

Example 52: N-(3-bromo-4-fluorophenyl)-4-((2-(sulfamoylamino)ethyl)amino)-1,2,5-oxadiazole-3-carboximidamide Step 1: N-(1-(4-bromophenyl)cyclobutyl)-4-fluorobenzamide To a stirred solution of 1-(4-bromophenyl)cyclobutanamine (300 mg, 1.327 mmol) in DMF (10 mL) were added 4-fluorobenzoic acid (223 mg, 1.592 mmol), Et$_3$N (0.56 mL, 4.02 mmol) and HATU (605 mg, 1.592 mmol) at RT and the reaction was stirred at RT for 15 h. The solvent was concentrated and water (20 mL) was added to the mixture which was extracted with EtOAc (30 mL×2). The organic layers were collected, washed with brine (20 mL), dried over Na$_2$SO$_4$, filtered, and the filtrate was concentrated in vacuo. The residue was purified by silica gel chromatography to give the title compound as a solid. MS (ESI) m/z: 347.9 [M+H$^+$].

Step 2: 4-fluoro-N-(1-(4-(4,4,5,5-tetramethyl-1,3,2-dioxaborolan-2-yl)phenyl)cyclobutyl)benzamide To a stirred solution of N-(1-(4-bromophenyl)cyclobutyl)-4-fluorobenzamide (146 mg, 0.419 mmol) in 1,4-dioxane (10 mL) were added 4,4,4',4',5,5,5',5'-octamethyl-2,2'-bi(1,3,2-dioxaborolane) (128 mg, 0.503 mmol), potassium acetate (123 mg, 1.258 mmol) and Pd(dppf)Cl$_2$ (31 mg, 0.042 mmol) at RT and the mixture was subjected to the usual Suzuki coupling and workup conditions. The crude was purified by silica gel chromatography to give the title compound as a solid. MS (ESI) m/z: 396.1 [M+H$^+$].

Step 3: 4-fluoro-N-(1-(4-(4-(2-hydroxypropan-2-yl)-6-(trifluoromethyl)pyridin-3-yl)phenyl)cyclobutyl)benzamide To a stirred solution of 4-fluoro-N-(1-(4-(4,4,5,5-tetramethyl-1,3,2-dioxaborolan-2-yl)phenyl)cyclobutyl)benz-

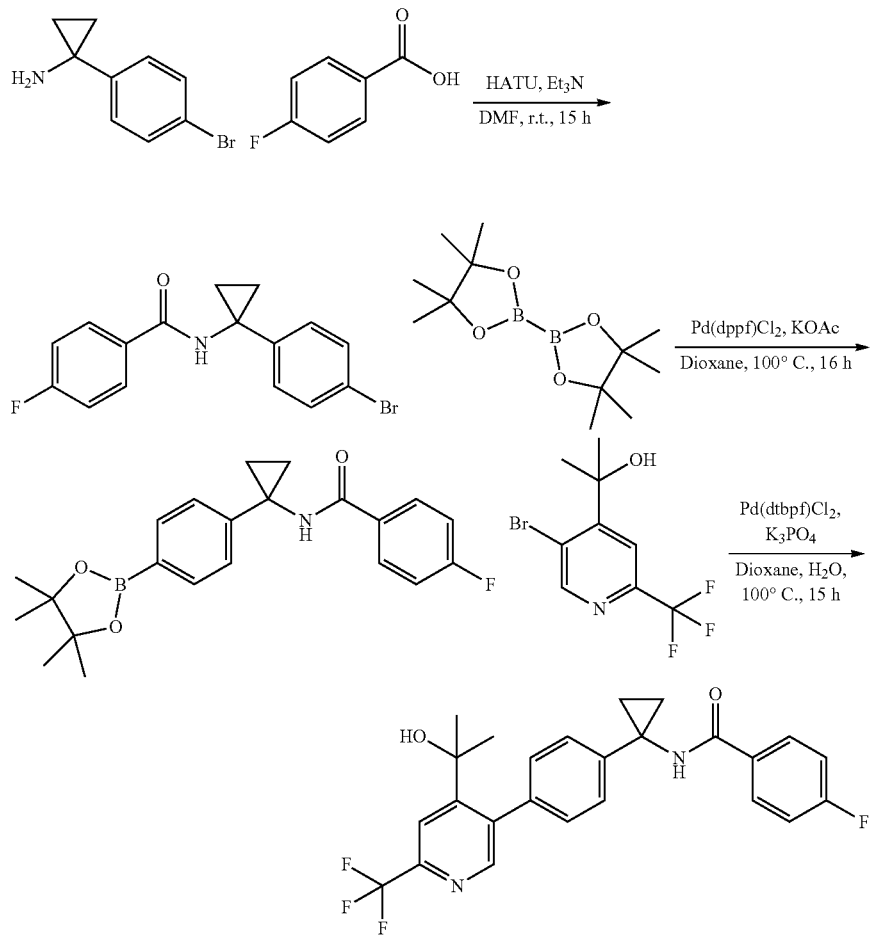

amide (50 mg, 0.126 mmol) in 1,4-dioxane (2.5 mL) and water (0.5 mL) were added Pd(dtbpf)Cl$_2$ (10 mg, 0.015 mmol), 2-(5-bromo-2-(trifluoromethyl)pyridin-4-yl)propan-2-ol (40 mg, 0.141 mmol) and K$_3$PO$_4$ (81 mg, 0.379 mmol) at RT and the mixture was subjected to the usual Suzuki coupling and workup conditions. The crude was purified by reversed phase HPLC on a GILSON 281 instrument fitted with a Waters Xbridge Prep OBD C18 column (100×19 mm×5 um) using water (0.225% formic acid)-ACN as mobile phases to afford the title compound as a solid. $^1$H NMR (400 MHz, CD$_3$OD) δ 9.1 (s, 1 H), 8.3 (s, 1 H), 8.3 (s, 1 H), 7.9 (dd, 2 H), 7.6 (d, 2 H), 7.3 (d, 2 H), 7.2 (t, 2 H), 2.7 (t, 4 H), 2.1-2.2 (m, 1 H), 2.0-2.1 (m, 1 H), 1.3 (s, 6 H). MS (ESI) m/z: 473.2 [M+H$^+$].

Example 53: 4-fluoro-N-(1-(4-(4-(hydroxymethyl)-6-(trifluoromethyl)pyridin-3-yl)phenyl)cyclobutyl)benzamide

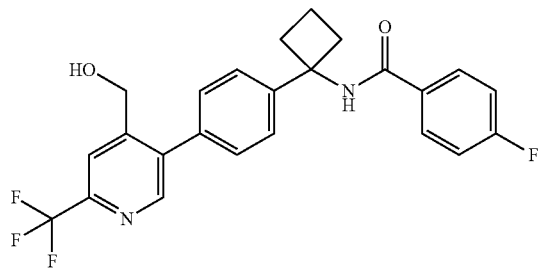 [SMILES: O=C(NC1(c2ccc(-c3cnc(C(F)(F)F)cc3CO)cc2)CCC1)c1ccc(F)cc1]

The title compound was prepared in a similar fashion as Example 52. $^1$H NMR (500 MHz, CDCl$_3$) δ 8.57 (s, 1 H), 8.02 (s, 1 H), 7.81 (dd, 2 H), 7.62 (d, 2 H), 7.30 (d, 2 H), 7.12 (t, 2 H), 6.67 (s, 1 H), 4.74 (s, 2 H), 2.66-2.80 (m, 4 H), 2.18-2.26 (m, 1 H), 2.02-2.06 (m, 1 H). MS (ESI) m/z: 445.1 [M+H$^+$].

Example 54: N-(1-(4-(6-cyclopropoxy-4-(2-hydroxypropan-2-yl)pyridin-3-yl)phenyl)cyclobutyl)-4-fluorobenzamide

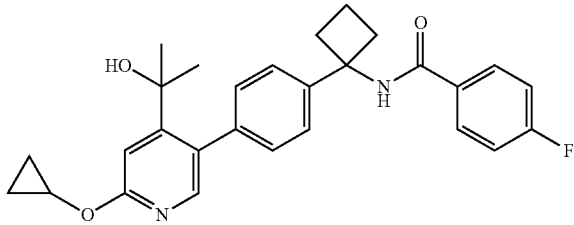 [SMILES: CC(C)(O)c1cc(OC2CC2)ncc1-c1ccc(C2(NC(=O)c3ccc(F)cc3)CCC2)cc1]

The title compound was prepared from 4-fluoro-N-(1-(4-(4,4,5,5-tetramethyl-1,3,2-dioxaborolan-2-yl)phenyl)cyclobutyl)benzamide and 2-(5-bromo-2-cyclopropoxypyridin-4-yl)propan-2-ol in a similar manner as Example 52. $^1$H NMR (400 MHz, CD3OD) δ 7.89 (dd, 2 H), 7.77 (s, 1 H), 7.75-7.79 (m, 1 H), 7.58 (d, 2 H), 7.46 (s, 1 H), 7.26 (d, 2 H), 7.18 (t, 2 H), 4.11-4.18 (m, 1 H), 2.71 (t, 4 H), 2.11-2.21 (m, 1 H), 1.95-2.07 (m, 1 H), 1.31 (s, 6 H), 0.82-0.90 (m, 2 H), 0.74-0.81 (m, 2 H). MS (ESI) m/z: 461.2 [M+H$^+$].

Examples 55-60: 4-fluoro-N-(1-(4'-(2-hydroxypropan-2-yl)-6'-(trifluoromethyl)-[2,3'-bipyridin]-5-yl)-2-methylcyclopropyl)benzamide

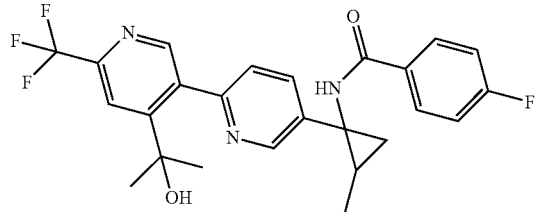 [SMILES: CC1CC1(NC(=O)c1ccc(F)cc1)c1ccc(-c2cnc(C(F)(F)F)cc2C(C)(C)O)nc1]

Step 1: 1-(6-chloropyridin-3-yl)-2-methylcyclopropanamine

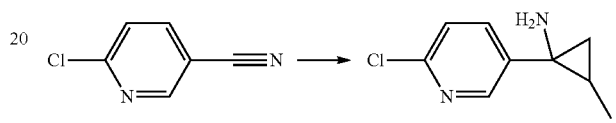

To a flask that was thoroughly purged with nitrogen and vacuumed three times was added a solution of 6-chloronicotinonitrile (200.00 mg, 1.443 mmol) in THF (4.00 ml). The mixture was cooled to −78° C. and titanium isopropoxide (0.893 ml, 3.02 mmol) was added and the mixture was stirred for 15 min. To this stirred solution was added propylmagnesium chloride (1.941 ml, 3.88 mmol) and the mixture was allowed to warm to RT and stirred overnight. The reaction mixture was quenched with aq. 1N NaOH and then extracted with EtOAc. The organic layer was collected, dried over anhydrous MgSO$_4$, filtered and the filtrate was concentrated under reduced pressure. The title compound was obtained as an oil and used in the next step directly. MS (ESI) m/z: 183.1 [M+H]$^+$.

Step 2: N-(1-(6-chloropyridin-3-yl)-2-methylcyclopropyl)-4-fluorobenzamide

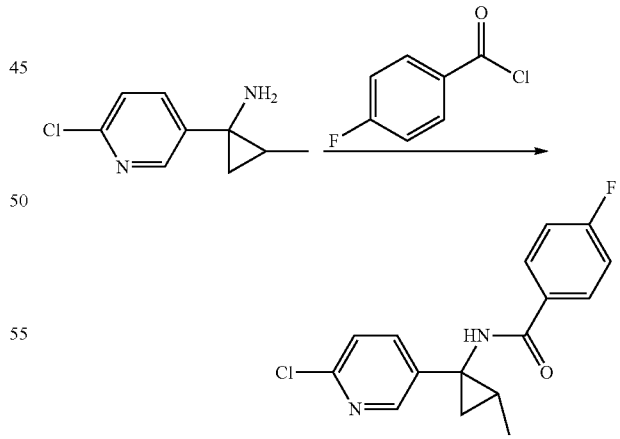

To a solution of 1-(6-chloropyridin-3-yl)-2-methylcyclopropanamine (262.00 mg, 1.434 mmol) in DCM (3.00 ml) at 0° C. were added DIEA (0.752 ml, 4.30 mmol) and 4-fluorobenzoyl chloride (0.085 ml, 0.717 mmol). The mixture was stirred at 0° C. for 1 h, diluted with sat. NaHCO$_3$, and extracted with EtOAc. The organic layer was separated, washed with brine, dried over anhydrous MgSO$_4$, filtered and concentrated. The residue was purified by flash chromatography (0-50% EtOAc/hexanes) to give the title compound as a solid. MS (ESI) m/z: 305.1 [M+H]⁺.

Step 3: (5-(1-(4-fluorobenzamido)-2-methylcyclopropyl) pyridin-2-yl)boronic acid

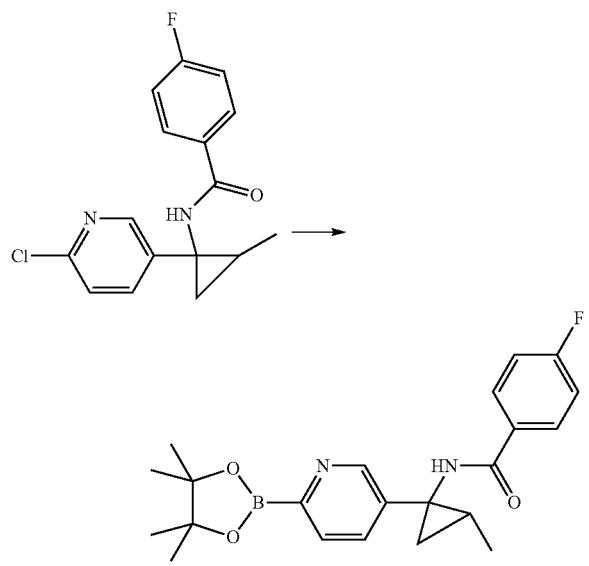

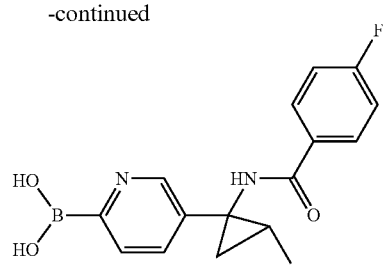

To a vial were added N-(1-(6-chloropyridin-3-yl)-2-methylcyclopropyl)-4-fluorobenzamide (124.00 mg, 0.407 mmol), bis(pinacolato)diboron (155 mg, 0.610 mmol), 1,1'-bis(di-tert-butylphosphino)ferrocene palladium dichloride (39.8 mg, 0.061 mmol) and potassium acetate (120 mg, 1.221 mmol). The vial was purged with nitrogen and then dioxane (2 mL) was added. The vial was again thoroughly purged with nitrogen and then allowed to stir at 75° C. for 6 h. The reaction mixture was filtered and the filtrate was concentrated. The residue was co-evaporated with hexane (2×) and vacuum dried to afford the title compound which was used in the next step without further purification. MS (ESI) m/z: 315.1[M+H]⁺.

Step 4: 4-fluoro-N-(1-(4'-(2-hydroxypropan-2-yl)-6'-(trifluoromethyl)-[2,3'-bipyridin]-5-yl)-2-methylcyclopropyl) benzamide

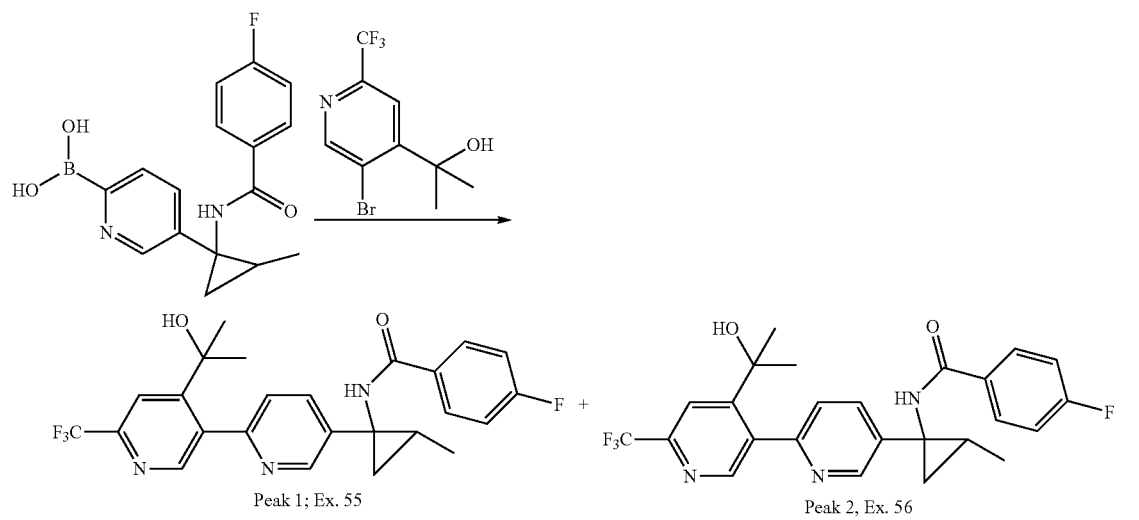

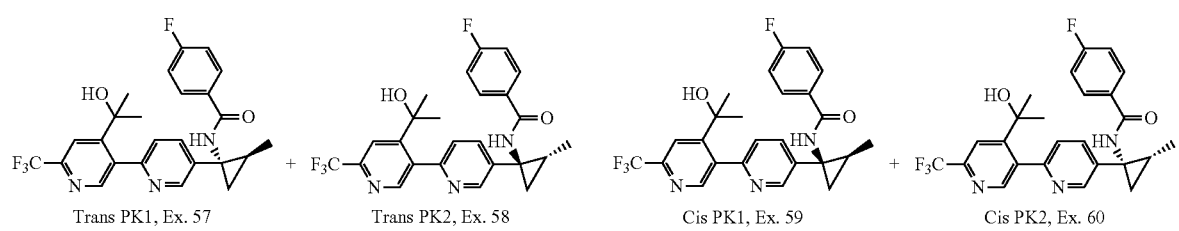

To a vial equipped with a stir bar were added (5-(1-((tert-butoxycarbonyl)amino)cyclopropyl)pyridin-2-yl)boronic acid, 2-(5-bromo-2-(trifluoromethyl)pyridin-4-yl)propan-2-ol (116 mg, 0.407 mmol), 1,1'-bis(di-tert-butylphosphino)ferrocene palladium dichloride (39.8 mg, 0.061 mmol), sodium carbonate (0.611 ml, 1.222 mmol) and dioxane (2 mL). The vial was thoroughly flushed with nitrogen and then subjected to microwave irradiation at 130° C. The reaction mixture was cooled, diluted with EtOAc and washed with sat. NaHCO$_3$. The organic layer was separated, washed with water and brine, dried over MgSO$_4$, filtered and the filtrate was concentrated under reduced pressure. The oil obtained was first purified on a silica gel column to give a crude material which was further purified by reversed phase HPLC using ACN/Water (0.1% TFA) as eluents. Peak 1 was assigned as the trans-isomer and Peak 2 as the cis-isomer. Absolute stereochemistry was not determined.

Peak 1 (Ex. 55) and Peak 2 (Ex. 56) were then separately resolved by SFC purification to give Peak A-trans and Peak B-trans, and Peak C-cis and Peak D-cis.

P1-A (TRANS) (Ex. 57): 4-fluoro-N-((1S,2S)-1-(4'-(2-hydroxypropan-2-yl)-6'-(trifluoromethyl)-[2,3'-bipyridin]-5-yl)-2-methylcyclopropyl)benzamide.
MS (ESI) m/z: 474.1 [M+H]$^+$.
$^1$H NMR (499 MHz, DMSO-d$_6$) δ 9.11 (s, 1H), 8.48 (d, 2H), 8.17 (s, 1H), 8.07-7.95 (m, 2H), 7.68 (d, 1H), 7.49 (d, 1H), 7.34 (t, 2H), 1.80-1.64 (m, 1H), 1.58-1.39 (m, 2H), 1.28 (s, 3H), 1.23 (d, 7H), 1.13 (d, 1H).

P1-B (TRANS) (Ex. 58): 4-fluoro-N-((1R,2R)-1-(4'-(2-hydroxypropan-2-yl)-6'-(trifluoromethyl)-[2,3'-bipyridin]-5-yl)-2-methylcyclopropyl)benzamide.
MS (ESI) m/z: 474.1 [M+H]$^+$.
$^1$H NMR (499 MHz, DMSO-d$_6$) δ 9.12 (s, 1H), 8.48 (d, 2H), 8.18 (s, 1H), 8.02 (d, 2H), 7.69 (d, 1H), 7.49 (d, 1H), 7.34 (t, 2H), 1.81-1.65 (m, 1H), 1.54-1.44 (m, 1H), 1.28 (d, 6H), 1.23 (s, 3H), 1.17-1.12 (m, 2H).

P2-C (CIS) (Ex. 59): 4-fluoro-N-((1S,2S)-1-(4'-(2-hydroxypropan-2-yl)-6'-(trifluoromethyl)-[2,3'-bipyridin]-5-yl)-2-methylcyclopropyl)benzamide.
MS (ESI) m/z: 474.1 [M+H]$^+$.
$^1$H NMR (499 MHz, DMSO-d$_6$) δ 9.38 (s, 1H), 8.73 (s, 1H), 8.54 (s, 1H), 8.19 (s, 1H), 7.96 (d, 3H), 7.56 (s, 1H), 7.31 (d, 3H), 1.41 (d, 3H), 1.25 (d, 6H), 0.86 (d, 3H).

P2-D (CIS) (Ex. 60): 4-fluoro-N-((1S,2R)-1-(4'-(2-hydroxypropan-2-yl)-6'-(trifluoromethyl)-[2,3'-bipyridin]-5-yl)-2-methylcyclopropyl)benzamide.
MS (ESI) m/z: 474.1 [M+H]$^+$.
$^1$H NMR (499 MHz, DMSO-d$_6$) δ 9.40 (s, 1H), 8.73 (s, 1H), 8.54 (s, 1H), 8.19 (s, 1H), 8.10-7.96 (m, 1H), 7.96-7.84 (m, 2H), 7.55 (d, 1H), 7.36-7.24 (m, 2H), 5.83-5.66 (m, 1H), 1.71-1.53 (m, 1H), 1.43 (s, 1H), 1.25 (s, 7H), 0.87 (s, 3H).

Biological Assays

IDO1 Cellular Assay in HeLa Cells Stimulated with IFNγ

HeLa cells were cultured in complete HeLa culture medium (90% EMEM, 10% heat-inactivated fetal bovine serum) and expanded to about 1×10$^9$ cells. The cells were then collected and frozen down at 1×10$^7$ cells/vial in 1 mL frozen medium (90% complete HeLa culture medium, 10% DMSO).

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen HeLa cells were thawed and transferred into HeLa assay medium (99% complete HeLa culture medium, 1% Pen/Strep) with 20 mL medium/vial of cells. The cells were spun down at 250 g in a table top centrifuge for 5 min and suspended in same volume of HeLa assay medium. The cells were then counted and adjusted to a density of 2×10$^5$ cells/mL in HeLa assay medium. Sterile L-tryptophan were added to the cells with final concentration of 300 uM L-tryptophan. A small aliquot (2 mL/plate) of HeLa cells were set aside and were not treated with IFNγ, to serve as the Max-E control. The rest of HeLa cells were added with sterile IFNγ (Cat #285-IF, R & D systems) with a final concentration of 100 ng/mL.

HeLa cells with and without IFNγ were dispensed to the respective wells of 384-well assay plates containing the compounds. The plates were incubated for about 48 hours at a 37° C., 5% CO$_2$ incubator. Afterwards, 12 μL of 0.5 M methyl isonipecotate in dimethyl sulfoxide were added into each well and the plates were sealed and incubated at 37° C. without CO$_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic IC$_{50}$ equation.

The biological activity data using the IDO1 cellular assay described above are summarized in the table below. Compounds disclosed herein generally have IC$_{50}$ of about 0.1 nM to about 10,000 nM, or more specifically, about 1 nM to about 10,000 nM, or more specifically, about 2 nM to about 5,000 nM, or more specifically, about 5 nM to about 1,000 nM, or still more specifically, about 10 nM to about 500 nM. Specific IC$_{50}$ activity data for the exemplified compounds disclosed herein is provided in the following table.

IDO1 Human Whole Blood Assay

Compounds to be tested were serially diluted in ten 3-fold steps in DMSO starting from 10 mM. 3 μL of compound dilutions or DMSO alone were then dispensed from the dilution plate into a polypropylene 96-well assay plate containing 97 μL of RPMI using an Echo 555 acoustic liquid handler (Labcyte). LPS and IFNγ was prepared in in RPMI to a 10× of final conc. (1000 ng/mL), final concentration is 100 ng/mL.

Human whole blood was drawn in sodium heparin coated tubes from healthy internal donors. 240 μL of blood was transferred to each of the wells of a v-bottom 96 well plate. 30 μL of compound was transferred from intermediate dilution plate, and incubated for 15 min. 30 μL from stimulants was then transferred to blood and mixed thoroughly. Plate was covered with breathable membrane and incubated at 37° C. for overnight (18 h).

On day 2 isotope labeled standard of kynurenine and tryptophan was made in water at 10× concentration and 30 μL was added to the blood at 3 μM final concentration. The assay plates were centrifuged at 300×G for 10 min with no brake to separate plasma from red blood cells. 60 μL of plasma samples was removed without disturbing red blood cells. Plasma was diluted with RPMI in 1:1 ratio and proteins were precipitated out with two volume of Acetonitrile. The plates were centrifuged at 4000×G for 60 min. 20 μL of supernatant was carefully transferred to a 384 well plate contain 40 μL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadrupole MS/MS instrument. For each sample, 5 µL were injected onto an Atlantis T3 column (2.1 mm×150 mm, 3 µm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data was acquired in positive mode using a HESI interface. The operational parameters for the TSQ Quantum Ultra instrument were a spray voltage of 4000 V, capillary temperature of 380° C., vaporizer temperature 400° C., sheath gas 60 arbitrary units, Aux gas 20 arbitrary units, tube lens 85 and collision gas 1.2 mTorr. SRM chromatograms of kynurenine (Q1: 209.2>Q3:94.0) and internal standard (Q1: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and $IC_{50}$ values. Compounds were titrated and $IC_{50}$'s were calculated by 4 parameter sigmoidal curve fitting formula.

The biological activity data of selective compounds using the IDO1 human whole blood assay described above are summarized in the table below.

| Ex. # | HeLa Cell Potency, $IC_{50}$ (nM) | Human Whole Blood Potency, $IC_{50}$ (nM) |
|---|---|---|
| 1 | 3.8 | |
| 2 | 3.7 | |
| 3 | 5.2 | |
| 4 | 7.1 | |
| 5 | 18.2 | |
| 6 | 36.6 | |
| 7 | 4.4 | 398 |
| 8 | 2,825 | |
| 9 | 19.1 | |
| 10 | 445.1 | |
| 11 | 3.0 | |
| 12 | 2.1 | 246 |
| 13 | 14.6 | |
| 14 | 67.7 | |
| 15 | 318.6 | |
| 16 | 17.1 | |
| 17 | 153.0 | |
| 18 | 197.5 | |
| 19 | 10,000 | |
| 20 | 18.5 | |
| 21 | 30.2 | |
| 22 | 10,000 | |
| 23 | 116.2 | |
| 24 | 316.2 | |
| 25 | 9.9 | 587 |
| 26 | 45.5 | |
| 27 | 95.2 | |
| 28 | 31.7 | |
| 29 | 28.5 | |
| 30 | 4.4 | |
| 31 | 15.1 | |
| 31 | 136.1 | |
| 33 | 8.9 | |
| 34 | 295.8 | |
| 35 | 8.2 | 1066 |
| 36 | 1.9 | 308 |
| 37 | 120.3 | |
| 38 | 6.1 | |
| 39 | 12.6 | |
| 40 | nd | |
| 41 | 8.4 | |
| 42 | 4.9 | 392 |
| 43 | 524.0 | |
| 44 | 308.3 | |
| 45 | 1.5 | |
| 46 | 2.1 | 703.3 |
| 47 | 2.1 | 126.7 |
| 48 | 4.2 | 922.1 |
| 49 | 2.7 | 578.5 |
| 50 | 1.5 | 185.9 |
| 51 | 2.3 | 233.2 |
| 52 | 2.2 | 151.9 |
| 53 | 4.3 | 1000 |
| 54 | 2.2 | 336.1 |
| 55 | 26.5 | |
| 56 | 8.3 | 361.1 |
| 57 | 41.7 | |
| 58 | 9.9 | 284.1 |
| 59 | 4.9 | 171 |
| 60 | 3.8 | 210.5 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I), or a pharmaceutically acceptable salt thereof:

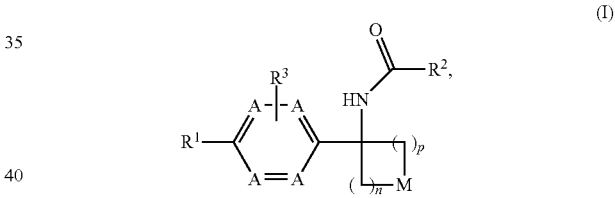

(I)

wherein:

n is 1;

p is selected from 0 and 1;

each occurrence of A is independently selected from —CH= and —N=, provided that at least one A is —CH=;

M is selected from —O—, —S— and —$CR^aR^b$—, each of $R^a$ and $R^b$ is independently selected from H, halogen, —OH, and —$C_{1-8}$ alkyl; or alternatively, $R^a$ and $R^b$ together with the carbon to which they are attached form a $C_{3-4}$ carbocyclic ring, optionally substituted with 1-2 substituents independently selected from halogen and $C_{1-4}$ alkyl;

$R^1$ is selected from:

(1) phenyl, and (2) a 6-membered monocyclic heterocyclyl;

wherein each of the phenyl of (1) and the heterocyclyl of (2) is optionally substituted with 1-3 substituents independently selected from:

(a) halogen, (b) —$C_{3-8}$ cycloalkyl, optionally substituted with —OH, (c) —CN, (d) —O—$C_{1-8}$ alkyl, optionally substituted with 1-5 halogens, (e) —O—$C_{3-8}$ cycloalkyl,
(f) —$C_{1-8}$ alkyl, optionally substituted with 1-4 substituents independently selected from halogen, —OH, —$NH_2$, $NHC(O)R^c$, and —$S(O)_2$—$C_{1-8}$ alkyl, wherein $R^c$ is selected from —$C_{1-8}$ alkyl and —$C_{3-8}$ cycloalkyl,
(g) —NH—$S(O)_2$—$R^c$, wherein $R^c$ is selected from —$C_{1-8}$ alkyl and —$C_{3-8}$ cycloalkyl,
(h) —C(O)—OH,
(i) aryl, optionally substituted with 1-3 halogens and
(j) heterocyclyl, optionally substituted with 1-3 substituents independently selected from halogen and —$C_{1-8}$ alkyl;
$R^2$ is selected from:
(1) $C_{3-8}$ carbocyclyl, and
(2) aryl,
wherein each of the $C_{3-8}$ carbocyclyl of (1), and the aryl of (2) is optionally substituted with 1-3 substituents independently selected from:
(a) halogen,
(b) —$C_{3-8}$ cycloalkyl,
(c) —CN,
(d) —O—$C_{1-8}$ alkyl, optionally substituted with 1-3 halogens and
(e) —$C_{1-8}$ alkyl, optionally substituted with 1-3 substituents independently selected from halogen, —OH, and —$NH_2$; and
$R^3$ is selected from H, halogen and —$C_{1-8}$ alkyl.

2. The compound of claim 1, or a pharmaceutically acceptable salt thereof,
wherein:
n is 1;
p is 0 or 1;
M is selected from —O— and —$CR^aR^b$—, each of $R^a$ and $R^b$ is independently selected from H, halogen, —OH and —$C_{1-6}$ alkyl;
$R^1$ is selected from:
(1) phenyl, and
(2) a 6-membered monocyclic heterocyclyl;
wherein each of the phenyl of (1) and the heterocyclyl of (2) is optionally substituted with 1-3 substituents independently selected from:
(a) halogen,
(b) —$C_{3-6}$ cycloalkyl, optionally substituted with —OH,
(c) —CN,
(d) —O—$C_{1-6}$ alkyl, optionally substituted with 1-3 halogens,
(e) —O—$C_{3-6}$ cycloalkyl,
(f) —$C_{1-6}$ alkyl, optionally substituted with 1-4 substituents independently selected from halogen, —OH, —$NH_2$, $NHC(O)R^c$, and —$S(O)_2$—$C_{1-6}$ alkyl, wherein $R^c$ is selected from —$C_{1-6}$ alkyl and —$C_{3-6}$ cycloalkyl,
(g) —NH—$S(O)_2$—$R^c$, wherein $R^c$ is selected from —$C_{1-6}$ alkyl and —$C_{3-6}$ cycloalkyl,
(h) —C(O)—OH, and
(i) heterocyclyl, optionally substituted with 1-3 substituents independently selected from halogen and —$C_{1-6}$ alkyl;
$R^2$ is selected from:
(1) $C_{3-6}$ carbocyclyl, and
(2) aryl,
wherein each of the $C_{3-6}$ carbocyclyl of (1), and the aryl of (2) is optionally substituted with 1-3 substituents independently selected from:
(a) halogen,
(b) —$C_{3-6}$ cycloalkyl,
(c) —CN,
(d) —O—$C_{1-6}$ alkyl, optionally substituted with 1-3 halogens, and
(e) —$C_{1-6}$ alkyl, optionally substituted with 1-3 substituents independently selected from halogen, —OH, and —$NH_2$; and
$R^3$ is selected from H and halogen.

3. The compound of claim 1, or a pharmaceutically acceptable salt thereof, wherein:
n is 1;
p is 0 or 1;
each A group is —CH═;
or alternatively, one A group is —N═ and the three other A groups are each —CH═; and
M is selected from —O—, —$CH_2$—, —$CF_2$—, and —$CH(CH_3)$—.

4. The compound of claim 1, or a pharmaceutically acceptable salt thereof, wherein $R^3$ is selected from H and halogen.

5. The compound of claim 1, or a pharmaceutically acceptable salt thereof, wherein:
$R^1$ is selected from:
(1) phenyl, and
(2) a 6 membered monocyclic heterocyclyl containing one to three heteroatoms independently selected from N, O, and S;
wherein each of the phenyl of (1) and the mono-cyclic heterocyclyl of (2) is optionally substituted with 1-3 substituents independently selected from:
(a) halogen,
(b) —$C_{3-6}$ cycloalkyl optionally substituted with —OH,
(c) —CN,
(d) —O—$C_{1-6}$ alkyl, optionally substituted with 1-3 halogens,
(e) —O—$C_{3-6}$ cycloalkyl,
(f) —$C_{1-6}$ alkyl, optionally substituted with 1-4 substituents independently selected from halogen, —OH, and —$S(O)_2$—$C_{1-6}$ alkyl,
(g) —NH—$S(O)_2$—$R^c$, wherein $R^c$ is selected from —$C_{1-6}$ alkyl and —$C_{3-6}$ cycloalkyl,
(h) —C(O)—OH, and
(i) a 5-6 membered monocyclic ring containing one to three heteroatoms independently selected from N, O, and S, optionally substituted with —$C_{1-6}$ alkyl.

6. The compound of claim 1, or a pharmaceutically acceptable salt thereof, wherein:
$R^1$ is a 6 membered monocyclic heterocyclyl selected from pyrazinyl, pyridazinyl, pyridinyl, and pyrimidinyl; optionally substituted with 1-3 substituents independently selected from:
(a) halogen,
(b) cyclopropyl, optionally substituted with —OH,
(c) cyclobutyl, optionally substituted with —OH,
(d) —CN,
(e) —O—$C_{1-3}$ alkyl, optionally substituted with 1-3 halogens,
(f) —O-cyclopropyl,
(g) —$C_{1-4}$ alkyl, optionally substituted with 1-4 substituents independently selected from halogen, —OH and —$S(O)_2$—$C_{1-4}$ alkyl,
(h) —C(O)—OH, and
(i) 1,2,4-oxadiazolyl, optionally substituted with —$C_{1-4}$ alkyl.

7. The compound of claim 1, or a pharmaceutically acceptable salt thereof, wherein:

R² is selected from:
(1) C₃₋₆ carbocyclyl, and
(2) phenyl;
wherein each of the C₃₋₆ carbocyclyl of (2) and the phenyl of (3) is optionally substituted with 1-3 substituents independently selected from:
(a) halogen,
(b) —C₃₋₆ cycloalkyl,
(c) —CN, and
(d) —C₁₋₄ alkyl, optionally substituted with 1-3 substituents independently selected from halogen and —OH.

8. The compound of claim 1, or a pharmaceutically acceptable salt thereof, wherein:
R² is selected from:
(1) 5-6 membered bridged bicyclic carbocyclyl, and
(2) phenyl;
wherein each of the 5-6 membered carbocyclyl of (1) and the phenyl of (2) is optionally substituted with 1-3 substituents independently selected from:
(a) halogen,
(b) —CN, and
(c) —C₁₋₄ alkyl, optionally substituted with 1-3 halogens.

9. The compound of claim 1, or a pharmaceutically acceptable salt thereof, wherein:
n is 1;
p is 0 or 1;
each A group is —CH=;
or alternatively, one A group is —N= and the three other A groups are each —CH=;
M is selected from —O—, —CH₂—, —CF₂—, and —CH(CH₃)—;
R¹ is selected from:
(1) phenyl, and
(2) a 6 membered monocyclic heterocyclyl containing one to three heteroatoms independently selected from N, O, and S;
wherein each of the phenyl of (1) and the mono-cyclic heterocyclyl of (2) is optionally substituted with 1-3 substituents independently selected from:
(a) halogen,
(b) —C₃₋₆ cycloalkyl, optionally substituted with —OH,
(c) —CN,
(d) —O—C₁₋₆ alkyl, optionally substituted with 1-3 halogens,
(e) —O—C₃₋₆ cycloalkyl,
(f) —C₁₋₆ alkyl, optionally substituted with 1-4 substituents independently selected from halogen, —OH, and —S(O)₂—C₁₋₆ alkyl,
(g) —NH—S(O)₂—Rᶜ, wherein Rᶜ is selected from —C₁₋₆ alkyl and —C₃₋₆ cycloalkyl,
(h) —C(O)—OH, and
(i) a 5-6 membered monocyclic heterocyclyl containing one to three heteroatoms independently selected from N, O, and S, optionally substituted with —C₁₋₆ alkyl;
R² is selected from:
(1) C₃₋₆ carbocyclyl, and
(2) phenyl;
wherein each of the C₃₋₆ carbocyclyl of (2) and the phenyl of (3) is optionally substituted with 1-3 substituents independently selected from:
(a) halogen,
(b) —C₃₋₆ cycloalkyl,
(c) —CN, and
(d) —C₁₋₄ alkyl, optionally substituted with 1-3 substituents independently selected from halogen and —OH; and
R³ is selected from H and halogen.

10. The compound of claim 1, or a pharmaceutically acceptable salt thereof, wherein:
n is 1;
p is 0 or 1;
each A group is —CH=;
or alternatively, one A group is —N= and the three other A groups are each —CH=;
M is selected from —O—, —CH₂—, and —CH(CH₃)—;
R¹ is a 6 membered monocyclic heterocyclyl selected from pyrazinyl, pyridazinyl, pyridinyl, and pyrimidinyl; each of which is optionally substituted with 1-3 substituents independently selected from:
(a) halogen,
(b) cyclopropyl, optionally substituted with —OH,
(c) cyclobutyl, optionally substituted with —OH,
(d) —CN,
(e) —O—C₁₋₃ alkyl, optionally substituted with 1-3 halogens,
(f) —O-cyclopropyl,
(g) —C₁₋₄ alkyl, optionally substituted with 1-4 substituents independently selected from halogen, —OH and —S(O)₂—C₁₋₄ alkyl,
(h) —C(O)—OH, and
(i) 1,2,4-oxadiazolyl, optionally substituted with —C₁₋₄ alkyl;
R² is selected from:
(1) a 5-6 membered bridged bicyclic carbocyclyl, and
(2) phenyl;
wherein each of the 5-6 membered carbocyclyl of (1) and the phenyl of (2) is optionally substituted with 1-3 substituents independently selected from:
(a) halogen,
(b) —CN, and
(c) —C₁₋₄ alkyl, optionally substituted with 1-3 halogens; and
R³ is selected from H and halogen.

11. The compound of claim 1 having formula (Ii), or a pharmaceutically acceptable salt thereof,

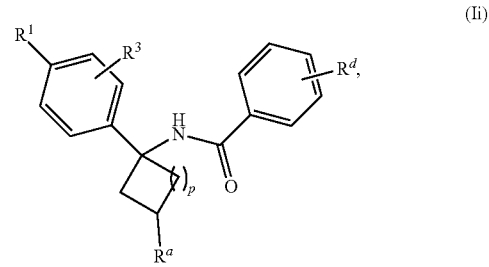

(Ii)

wherein:
p is 0 or 1;
R¹ is selected from:
(1) phenyl, and
(2) a 6 membered monocyclic heterocyclyl containing one to three heteroatoms independently selected from N, O, and S;
wherein each of the phenyl of (1) and the mono-cyclic heterocyclyl of (2) is optionally substituted with 1-3 substituents independently selected from:

(a) halogen,
(b) —C$_{3-6}$ cycloalkyl, optionally substituted with —OH,
(c) —CN,
(d) —O—C$_{1-6}$ alkyl, optionally substituted with 1-3 halogens,
(e) —O—C$_{3-6}$ cycloalkyl,
(f) —C$_{1-6}$ alkyl, optionally substituted with 1-4 substituents independently selected from halogen, —OH, and —S(O)$_2$—C$_{1-6}$ alkyl,
(g) —NH—S(O)$_2$—R$^c$, wherein R$^c$ is selected from —C$_{1-6}$ alkyl and —C$_{3-6}$ cycloalkyl,
(h) —C(O)—OH, and
(i) a 5-6 membered monocyclic heterocyclyl containing one to three heteroatoms independently selected from N, O, and S, optionally substituted with —C$_{1-6}$ alkyl;

R$^3$ is selected from H and halogen;
R$^a$ is selected from (a) H and (b) C$_{1-4}$ alkyl; and
R$^d$ is selected from:
(a) H,
(b) halogen, and
(c) —CN.

12. The compound of claim 11, or a pharmaceutically acceptable salt thereof, wherein:
p is 0 or 1;
R$^1$ is a 6 membered monocyclic heterocyclyl selected from pyrazinyl, pyridazinyl, pyridinyl, and pyrimidinyl; each of which is optionally substituted with 1-3 substituents independently selected from:
(a) halogen,
(b) cyclopropyl,
(c) —CN,
(d) —O—C$_{1-3}$ alkyl, optionally substituted with 1-3 halogens,
(e) —O-cyclopropyl,
(f) —C$_{1-4}$ alkyl, optionally substituted with 1-4 substituents independently selected from halogen, —OH, and —S(O)$_2$—C$_{1-4}$ alkyl,
(g) —NH—S(O)$_2$—C$_{1-4}$ alkyl,
(h) —NH—S(O)$_2$-cyclopropyl,
(i) —C(O)—OH, and
(j) 1,2,4-oxadiazolyl, optionally substituted with —C$_{1-4}$ alkyl;

R$^3$ is selected from H and halogen;
R$^c$ is selected from (a) H and (b) —CH$_3$; and
R$^d$ is selected from (a) halogen and (b) —CN.

13. The compound of claim 1, or a pharmaceutically acceptable salt thereof, selected from the group consisting of:
4-cyano-N-(1-(4-(6-methoxy-4-methylpyridin-3-yl)phenyl)cyclobutyl)benzamide,
4-cyano-N-(1-(4-(6-(difluoromethoxy)pyridin-3-yl)phenyl)cyclobutyl)benzamide,
4-cyano-N-(1-(4-(6-cyclopropoxypyridin-3-yl)phenyl)cyclobutyl)benzamide,
4-cyano-N-(1-(4-(6-cyclopropylpyridin-3-yl)-3-fluorophenyl)cyclobutyl)benzamide,
4-cyano-N-(1-(4-(6-cyclopropyl-4-methylpyridin-3-yl)-3-fluorophenyl)cyclobutyl)benzamide,
4-cyano-N-(1-(4-(5-(cyclopropanesulfonamido)pyridin-3-yl)phenyl)cyclobutyl)benzamide,
4-cyano-N-(1-(4-(2-cyclopropylpyrimidin-5-yl)phenyl)cyclobutyl)benzamide,
4-cyano-N-(1-(4-(6-(2-hydroxypropan-2-yl)pyridin-3-yl)phenyl)cyclobutyl)benzamide,
4-cyano-N-(1-(4-(4-methyl-6-(trifluoromethyl)pyridin-3-yl)phenyl)cyclobutyl)benzamide,
4-cyano-N-(1-(4-(6-cyclopropyl-4-methylpyridin-3-yl)phenyl)cyclobutyl)benzamide,
4-cyano-N-(1-(4-(6-cyclopropylpyridin-3-yl)phenyl)cyclobutyl)benzamide,
4-cyano-N-(1-(4-(6-cyanopyridin-3-yl)phenyl)cyclobutyl)benzamide,
4-cyano-N-(1-(4-(6-(1-hydroxyethyl)pyridin-3-yl)phenyl)cyclobutyl)benzamide,
4-cyano-N-(1-(4-(6-cyano-4-methylpyridin-3-yl)phenyl)cyclobutyl)benzamide,
4-cyano-N-(1-(4-(6-(3-methyl-1,2,4-oxadiazol-5-yl)pyridin-3-yl)phenyl)cyclobutyl)benzamide,
4-cyano-N-(1-(4-(6-(hydroxymethyl)-4-methoxypyridin-3-yl)phenyl)cyclobutyl)benzamide,
4-cyano-N-(1-(4-(6-((methylsulfonyl)methyl)pyridin-3-yl)phenyl)cyclobutyl)benzamide,
4-cyano-N-(1-(4-(6-(trifluoromethyl)pyridin-3-yl)phenyl)cyclobutyl)benzamide,
4-cyano-N-(1-(4-(6-(difluoromethyl)pyridin-3-yl)phenyl)cyclobutyl)benzamide,
5-(4-(1-(4-cyanobenzamido)cyclobutyl)phenyl)picolinic acid,
4-cyano-N-(1-(4-(6-(2,2,2-trifluoro-1-hydroxyethyl)pyridin-3-yl)phenyl)cyclobutyl)benzamide,
4-cyano-N-(1-(4-(6-(hydroxymethyl)pyridin-3-yl)phenyl)cyclobutyl)benzamide,
4-cyano-N-(1-(4-(6-cyclopropyl-2-(hydroxymethyl)pyridin-3-yl)phenyl)cyclobutyl)benzamide,
4-cyano-N-(1-(4-(5-cyclopropylpyrazin-2-yl)phenyl)cyclobutyl)benzamide,
4-cyano-N-(1-(4-(5-(2-fluoroethoxy)pyrazin-2-yl)phenyl)cyclobutyl)benzamide,
4-cyano-N-(1-(4-(6-isopropylpyridazin-3-yl)phenyl)cyclobutyl)benzamide,
4-cyano-N-(1-(4-(6-methoxy-4-(trifluoromethyl)pyridin-3-yl)phenyl)cyclobutyl)benzamide,
4-cyano-N-(1-(4-(6-methoxy-2-methylpyridin-3-yl)phenyl)cyclobutyl)benzamide,
N-(1-(4-(4,6-bis(trifluoromethyl)pyridin-3-yl)phenyl)cyclobutyl)-4-cyanobenzamide,
4-cyano-N-(1-(4-(6-(2-fluoroethoxy)pyridazin-3-yl)phenyl)cyclobutyl)benzamide,
4-cyano-N-(1-(4-(4-methoxy-6-(trifluoromethyl)pyridin-3-yl)phenyl)cyclobutyl)benzamide, cyano-N-(1-(4-(6-methoxy-5-(methylsulfonamido)pyridin-3-yl)phenyl)cyclobutyl)benzamide,
4-cyano-N-(1-(4-(4-(hydroxymethyl)-6-(trifluoromethyl)pyridin-3-yl)phenyl)cyclobutyl)benzamide,
4-cyano-N-(1-(4-(6-methoxy-2,4-dimethylpyridin-3-yl)phenyl)cyclobutyl)benzamide,
4-cyano-N-(1-(4-(4-cyano-6-(trifluoromethyl)pyridin-3-yl)phenyl)cyclobutyl)benzamide,
4-cyano-N-(1-(4-(6-(difluoromethoxy)-2,4-dimethylpyridin-3-yl)phenyl)cyclobutyl)benzamide,
4-cyano-N-(1-(4-(6-(difluoromethoxy)-4-methylpyridin-3-yl)phenyl)cyclobutyl)benzamide,
4-cyano-N-(1-(4-(4-formyl-6-isopropoxypyridin-3-yl)phenyl)cyclobutyl)benzamide,
4-cyano-N-(1-(4-(4-(difluoromethyl)-6-isopropoxypyridin-3-yl)phenyl)cyclobutyl)benzamide,
4-cyano-N-(1-(6'-cyclopropyl-4'-methyl-[3,3'-bipyridin]-6-yl)cyclobutyl)benzamide,
3-cyano-N-(1-(6'-(difluoromethoxy)-4'-methyl-[3,3'-bipyridin]-6-yl)cyclobutyl)bicyclo[1.1.1]-pentane-1-carboxamide, 3-cyano-N-(1-(6'-cyclopropyl-4'-methyl43,3'-bipyridin]-6-yl)cyclobutyl)bicyclo[1.1.1]pentane-1-carboxamide,
4-fluoro-N-(3-(4-(4-(hydroxymethyl)-6-(trifluoromethyl)pyridin-3-yl)phenyl)oxetan-3-yl)benzamide,
4-chloro-N-(1-(4-(4-(hydroxymethyl)-6-(trifluoromethyl)pyridin-3-yl)phenyl)cyclopropyl)benzamide,
N-(1-(4-(6-cyclopropoxy-4-(2-hydroxypropan-2-yl)pyridin-3-yl)phenyl)cyclopropyl)-4-fluorobenzamide,
N-(1-(4-(6-cyclopropoxy-4-(hydroxymethyl)pyridin-3-yl)phenyl)cyclopropyl)-4-fluorobenzamide,
4-fluoro-N-(1-(4-(4-(hydroxymethyl)-6-isopropoxypyridin-3-yl)phenyl)cyclopropyl)benzamide,
(S)-4-fluoro-N-(1-(4-(4-(1-hydroxyethyl)-6-(trifluoromethyl)pyridin-3-yl)phenyl)cyclopropyl)benzamide,
(R)-4-fluoro-N-(1-(4-(4-(1-hydroxyethyl)-6-(trifluoromethyl)pyridin-3-yl)phenyl)cyclopropyl)benzamide, 2,2,2-trifluoroacetate salt,
4-fluoro-N-(1-(4-(4-(hydroxymethyl)-6-(trifluoromethyl)pyridin-3-yl)phenyl)cyclobutyl)benzamide, and
N-(1-(4-(6-cyclopropoxy-4-(2-hydroxypropan-2-yl)pyridin-3-yl)phenyl)cyclobutyl)-4-fluorobenzamide.

14. A composition which comprises an inert carrier and a compound of claim 1 or a pharmaceutically acceptable salt thereof.

\* \* \* \* \*